United States Patent
Gu et al.

(10) Patent No.: US 6,207,157 B1
(45) Date of Patent: *Mar. 27, 2001

(54) **CONJUGATE VACCINE FOR NONTYPEABLE *HAEMOPHILUS INFLUENZAE***

(75) Inventors: Xin-Xing Gu, Rockville; Chao-Ming Tsai, Bethesda, both of MD (US); David J. Lim, Pasadena, CA (US); John B. Robbins, Chevy Chase, MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/842,409

(22) Filed: Apr. 23, 1997

Related U.S. Application Data (60) Provisional application No. 60/016,020, filed on Apr. 23, 1996.

(51) Int. Cl.[7] ............... A61K 39/00; A61K 38/43; A61K 38/48; A61K 39/385
(52) U.S. Cl. ............... 424/184.1; 42/92; 42/94; 42/94.63; 42/184.1; 42/197.11; 42/250.1; 42/251.1; 42/256; 42/256.1; 42/262.1; 435/71; 435/97; 435/197; 435/252.3
(58) Field of Search .................. 424/92, 94, 94.63, 424/197.11, 250.1, 251.1, 256, 256.1, 262.1; 435/7.1, 197, 97, 252.3, 732

(56) References Cited

U.S. PATENT DOCUMENTS

| | | | |
|---|---|---|---|
| 4,619,828 | * | 10/1986 | Gordon ................... 424/94 |
| 5,013,661 | * | 5/1991 | Munford et al. ............ 435/197 |
| 5,153,312 | | 10/1992 | Porro . |
| 5,204,098 | * | 4/1993 | Szu et al. ................. 424/92 |
| 5,506,139 | * | 4/1996 | Loosmore et al. ........... 435/252.3 |
| 5,601,831 | * | 2/1997 | Green et al. .............. 424/256.1 |
| 5,696,000 | * | 12/1997 | Krivan et al. ............. 435/732 |

FOREIGN PATENT DOCUMENTS

| | | | |
|---|---|---|---|
| 0245045 | * | 1/1987 | (EP) ................. A61K/39/385 |
| 0 245 045 A2 | | 11/1987 | (EP) . |
| 0 497 525 A2 | | 5/1992 | (EP) . |

OTHER PUBLICATIONS

Barenkamp, S. 1996. Immunization with High–Molecular–Weight Adhesion Proteins of Nntypeable *Haemophilus influenzae* Modifies Experimental Otitis Media in Chinchillas. Infection and Immunity. 64 (4): 1246–1251.*

Green et al. 1994. Nontypeable *Haemophilus influenzae* Lipo–oligosacchrides conjugates as Vaccine candidates against NTHi. Vaccines. pp. 12–129.*

Erwin et al. 1991. Infection and Immunity. 59(6): 1881–1887.*

Green et al. 1994. Vaccine. 94:125–129.*

Gu et al. 1995. Infection and Immunity. 63(10): 4115–4120.*

Gu et al. 1996. Infection and Immunity. 64(10): 4047–4053.*

Patrick et al. 1987. Infection and Immunity. 55(12): 2902–2911.*

(List continued on next page.)

Primary Examiner—Jennifer Graser
Assistant Examiner—Ja-Na A. Hines
(74) Attorney, Agent, or Firm—Knobbe, Martens, Olson & Bear, LLP (57) ABSTRACT

A conjugate vaccine for Nontypeable *Haemophilus influenzae* comprising lipooligosaccharide from which esterified fatty acids have been removed conjugated to an immunogenic carrier. The vaccine is useful for prevention of otitis media and respiratory infections in mammals.

20 Claims, 5 Drawing Sheets

OTHER PUBLICATIONS

Gibson et al. 1993. J. of Bacter. 175(0): 2702–2712.*

Helander et al. 1988. Eur. J. of Biochem. 177:483–492.*

Kondau et al. 1996. Infect. and Immun. 64(7): 2709–2715.*

Phillips et al. 1992. Biochem. 31:4515–4526.*

S.J. Barenkamp, M.D., et al., "Development of serum bactericidal activity following nontypable *Haemophilus influenzae* acute otitis media," *Pediatr. Infect. Dis. J.* 9(5):333–339 (1990).

S.J. Barenkamp, M.D., et al., "Immunization with High-–Molecular–Weight Adhesion Proteins of Nontypeable *Haemophilus influenzae* Modifies Experimental Otitis Media in Chinchillas," *Infection and Immuntiy* 64(4):1246–1251 (1996).

S. Berman, M.D., "Otitis Media In Children," *The New England Journal of Medicine* 332(23):1560–1565 (1995).

W.J. Black et al., "ADP–Ribosyltransferase Activity of Pertussis Toxin and Immunomodulation by *Bordetella pertussis*," *Science* 240:656–659 (1988).

F.A. Boettcher, et al., "Blood Collection from the Transverse Sinus in the Chinchilla," *Laboratory Animal Science* 40(2):223–224 (1990).

A.A. Campagnari, et al., "Antigenic Diversity of Lipooligosaccharides of Nontypable *Haemophilus influenzae*," *Infection and Immunity* 55(4):882–887 (1987).

R.A. Deich, et al., "Recombinant Hybrids of *Haemophilus influenzae* Outer Membrane Lipoproteins PCP and PAL as Vaccine Candidates Against Nontypable H. Influenzae Disease," *Vaccine Research* 2(1):31–39.

T.F. DeMaria, et al., "Immunization with Outer Membrane Protein P6 from Nontypeable *Haemophilus influenzae* Induces Bactericidal Antibody and Affords Protection in the Chinchilla Model of Otitis Media," *Infection and Immunity* 64(12):5187–5192 (1996).

Carl E. Frasch, et al., "Protection Against Group B Meningococcal Disease." *The Journal of Experimental Medicine* 147:629–644 (1978).

C. Galanos, et al., "Galactosamine–induced sensitization to the lethal effects of endotoxin," *Proc. Natl. Acad. Sci. USA* 76(11):5939–5943 (1979).

G.S. Giebink, M.D., "Experimental Otitis Media Due to *Haemophilus influenzae* in the Chinchilla," *Elsevier Science Publishing Co., Inc.* pp. 73–80 (1982).

G.S. Giebink, M.D., "Prediction Of Serious Versus Purulent Otitis Media By Otoscopy And Tympanometry In An Animal Model," *Laryngoscope* 93:208–221 (1983).

B.A. Green, et al., "Chinchilla Model of Experimental Otitis Media for Study of Nontypable *Haemophilus influenzae* Vaccine Efficacy," *Methods in Enzymology* 235:59–69 (1994).

B.A. Green, et al., "Nontypeable *Haemophilus influenzae* Lipo–oligosaccharide Conjugates as Vaccine Candidates against NTHi," *Vaccines* 94:125–129 (1994).

X. Gu, et al., "Purification of Rough–Type Lipopolysaccharides of *Neisseria meningitidis* From Cells and Outer Membrane Vesicles in Spent Media," *Analytical Biochemistry* 196:311–318 (1991).

X. Gu, et al., "Quantitation and Biological Properties of Released and Cell–Bound Lipoologosaccharides from Nontypeable *Haemophilus influenzae*," *Infection and Immunity* 63(10):4115–4120 (1995).

X. Gu, et al., "Synthesis, Characterization, and Immunologic Properties of Detoxified Lipooligosaccharide from Nontypeable *Haemophilus influenzae* Conjugated to Proteins," *Infection and Immunity* 64(10):4047–4053 (1996).

J.M. Kyd. et al., "Enhanced Respiratory Clearance of Nontypeable *Haemophilus influenzae* following Mucosal Immunization with P6 in a Rat Model," *Infection and Immunity* 63(8):2931–2940 (1995).

J.L. McGehee, et al., "Effect of Primary Immunization on Pulmonary Clearance of Nontypable *Haemophilus influenzae*," *Am. J. Respir. Cell Mol. Biol.* 1:201–210 (1989).

A.M. Pappenheimer, Jr., et al., "An Immunological Study Of The Diphtheria Toxin Molecule," *Immunochemistry* 9:891–906 (1972).

C.C. Patrick, et al., "Antigenic Characterization of the Oligosaccharide Portion of the Lipoologosaccharide of Nontypable *Haemophilus influenzae*," *Infection and Immunity* 55(12)2902–2911 (1987).

P.A. Shurin, M.D., et al., "Bactericidal antibody and susceptibility to otitis media caused by nontypable strains of *Haemophilus influenzae*," *The Journal of Pediatrics* 97(3):364–369 (1980).

S.E. Stool, M.D., et al., "The impact of otitis media," *Pediatr. Infect. Dis. J.* 8(1):S11–S14 (1989).

W.E. Dick, Jr., et al., "Glycoconjugates of Bacterial Carbohydrate Antigens," *Contrib. Microbiol. Immunol.* 10:48–114 (1989).

H.D. Hochstein, et al., "Futher Developments of Limulus Amebocyte Lysate Test," *Bulletin of the Parenteral Drug Association* 27(3):139–148 (1973).

H.J. Jennings, et al., "N Propionylated Group B Menigococal Polysaccharide Mimics A Unique Epitope On Group B *Neisseria Meningitidis*," *J. Exp. Med.* 165:1207–1211 (1987).

H.A. Kemp, et al., "Studies on the detrimental effects of bivalent binding in a microtitration plate ELISA and possible remedies," *Journal of Immunological Methods* 94:65–72 (1986).

* cited by examiner

CONJUGATE VACCINE FOR NONTYPEABLE *HAEMOPHILUS INFLUENZAE*

CROSS-REFERENCE TO RELATED APPLICATIONS

This application claims priority under 35 U.S.C. § 119(e)(1) to U.S. Provisional Application Ser. No. 60/016,020, filed Apr. 23, 1996.

FIELD OF THE INVENTION

The present invention relates to conjugate vaccines for prevention of bacterial infections. More specifically, the invention relates to a conjugate vaccine for nontypeable *Haemophilus influenzae* comprising lipooligosaccharide from which esterified fatty acids have been removed linked to an immunogenic carrier.

BACKGROUND OF THE INVENTION

Nontypeable *Haemophilus influenzae* (NTHi) is a major causative agent for acute otitis media (middle ear infections) and respiratory infections. Acute otitis media and otitis media with effusion are common childhood diseases, second in frequency of occurrence only to the common cold (Stool et al., *Pediatr. Infect. Dis. Suppl.*, 8:S11–S14, 1989). The annual cost of the medical and surgical treatment of otitis media in the United States is estimated at between three and four billion dollars (Berman, *New Engl. J. Med.*, 332:1560–1565, 1995). Moreover, inappropriate antibiotic treatment of otitis media can lead to the emergence of multidrug-resistant bacterial strains. There is currently no vaccine available for prevention of NTHi infection.

Current efforts in developing an NTHi vaccine are focused on cell surface antigens such as outer membrane proteins and pili or fimbria (Kyd et al., *Infect. Immun.*, 63:2931–2940, 1995; Deich et al., *Vaccine Res.*, 2:31–39, 1995). Among these, the most promising is P6 protein which appears to be antigenically conserved and elicits the production of antibodies that are bactericidal in vitro. Lipooligosaccharide (LOS) is a major NTHi cell surface antigen. LOS contains both lipid A and oligosaccharide (OS) components. Because the lipid A component of LOS is toxic, it must be detoxified prior to conjugation to an immunogenic carrier.

Barenkamp et al. (*Pediafr. Infect. Dis. J.*, 9:333–339, 1990) demonstrated that LOS stimulated the production of bactericidal antibodies directed against NTHi. McGehee et al. (*Am. Journal Respir. Cell Biol.*, 1:201–210, 1989) showed that passive immunization of mice with monoclonal antibodies directed against LOS from NTHi enhanced the pulmonary clearance of NTHi.

Green et al. (*Vaccines*, 125–129, 1994) disclose an NTHi vaccine comprising a conjugate of NTHi OS and the mutant nontoxic diphtheria protein $CRM_{197}$. The lipid A moiety was removed from LOS by treatment with acid, followed by derivatizing the resulting OS with adipic acid dihydrazide (ADH) and coupling to $CRM_{197}$. Despite the showing of Barenkamp et al. that LOS stimulated production of bactericidal antibodies against NTHi, the conjugates of Green et al. were determined to be poorly immnunogenic after injection into mice. Moreover, the conjugates did not elicit bactericidal antibodies against NTHi.

Thus, there is a need for a vaccine effective against NTHi. The present invention satisfies this need.

SUMMARY OF THE INVENTION

One embodiment of the present invention is a conjugate vaccine for nontypeable *Haemophilus influenzae* (NTHi), comprising NTHi lipooligosaccharide from which esterified fatty acids have been removed (dLOS), and an immunogenic carrier covalently linked thereto. In another aspect of the present invention, the immunogenic carrier is a protein. Preferably, the protein is tetanus toxin/toxoid, NTH high molecular weight protein, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, or respiratory syncytial virus F and G protein. Most preferably, the protein is tetanus toxoid or NTHi high molecular weight protein.

The present invention also provides a conjugate vaccine for nontypeable *Haemophilus influenzae* (NTHi), comprising NTHi lipooligosaccharide from which esterified fatty acids have been removed (dLOS), and an immunogenic carrier covalently linked thereto via a linker. Preferably, the linker is adipic acid dihydrazide, e-aminohexanoic acid, chlorohexanol dimethyl acetal, D-glucuronolactone or p-nitrophenylamine; most preferably, the linker is adipic acid dihydrazide.

Another embodiment of the invention is isolated NTHi lipooligosaccharide detoxified by removal of ester-linked fatty acids therefrom.

The present invention also provides a pharmaceutical composition comprising the vaccine conjugates described above in a pharmaceutically acceptable carrier. The pharmaceutical composition may further comprise an adjuvant. Preferably, the adjuvant is alum.

Another embodiment of the invention is a method of preventing otitis media caused by NTHi in a mammal, comprising administering to the mammal an effective immunoprotective amount of the vaccine described above. Preferably, the mammal is a human. The route of administration may be intramuscular, subcutaneous, intraperitoneal, intraarterial, intravenous or intranasal; most preferably, the administering step is intramuscular. According to another aspect of this preferred embodiment, the effective dose is between about 10 µg and about 50 µg. The method may further comprise injecting between about 10 µg and about 25 µg at about 2 months and at about 13 months after the administering step. Alternatively, the method may further comprise injecting between about 10 µg and about 25 µg at about 2, 4 and 16 months after the administering step.

According to another aspect of the invention, there is provided a method of detoxifing lipooligosaccharide from NTHi, comprising removing ester-linked fatty acids therefrom. Preferably, the ester-linked fatty acids are removed by treating the LOS with hydrazine.

Still another aspect of the present invention is a method of making a conjugate vaccine against NTHi, comprising:

removing ester-linked fatty acids from NTHi lipooligosaccharide to produce dLOS; and covalently binding said dLOS to an immunogenic carrier.

Advantageously, the removing step comprises treatment with hydrazine. The method may further comprise the step of attaching dLOS to a linker and attaching the linker to the carrier. Preferably, the linker is adipic acid dihydrazide, ε-aminohexanoic acid, chlorohexanol dimethyl acetal, D-glucuronolactone or p-nitrophenylethyl amine; most preferably, the linkaer is adipic acid dihydrazide.

DETAILED DESCRIPTION OF THE INVENTION

A conjugate vaccine comprising NTHi LOS from which esterified fatty acids had been removed (detoxified LOS or DLOS) aqd either tetanus toxoid (TI) or high molecular weight outer membrane adhesion proteins (HMPs) from NTHi induced significant increases in anti-LOS IgG antibody levels in both mice and rabbits. The isolation of HMPs is described by Barenkamp et al. (*Infect. Immun.* 64:1246–1251, 1996), the entire contents of which are hereby incorporated by reference. The HMPs exemplified herein are a mixture of two polypeptide species having approximate molecular weights of 120 kDa and 125 kDa Additional HMPs having molecular weights of about 100 kDa are also described by Barenkamp et al. and are also contemplated for use in the present invention. Antigenicity of the two conjugates was similar to that of LOS. The antisera generated against the dLOS-TT and dLOS-HMP conjugates in rabbits was bactericidal against NTHi as determined by a complement-mediated cell lysis assay. The conjugates exhibited very low toxicity and were not pyrogenic in rabbits.

The dLOS-TT conjugate was studied in the chinchilla model of otitis media which is the art-recognized animal model for human otitis media The dLOS-TT conjugate vaccine successfully protected chinchillas from a challenge dose of the NTHi strain used to make the vaccine (strain 9274). Chinchillas received injections of dLOS-TT conjugate from NTHi 9274 and were then challenged by intrabullar inoculation of NTHi 9274. Infection developed in all of the control animals and 56% of the conjugate-immunized animals over a time period of three weeks. The incidence of both left ear and inner ear infection was reduced 51% in the conjugate group relative to the control group. Among infected animals, bacterial counts of the middle ear fluids were sigrificantly lower in conjugate-immunized animals than in control animals. All immunized animals responded with elevated serum titers of anti-LOS antibody and 49% demonstrated complement-mediated bactericidal activity against the homologous strain. Thus, active immunization with conjugates results in a significant in vivo reduction of the incidence of NTHi-induced otitis media in an art-recognized animal model of human otitis media.

Although the use of hydrazine for detoxification of LOS from NTHi is described herein, the use of any reagent or enzyme capable of removing ester-linked fatty acids from lipid A is within the scope of the present invention. Dried LOS from any strain of NTHi is suspended in liquid anhydrous hydrazine at a temperature of between 1° C. and 100° C.; preferably between 25° C. and 75° C.; more preferably, about 37° C. for a period between 1 hour and 24 hours, most preferably for a period of about 2–3 hours. After removal of ester-linked fatty acids, dLOS is conjugated to the linker adipic acid dihydrazide (ADH) prior to conjugation to the immunogenic carrier proteins TT or NTHI HMPs. Although ADH is the preferred linker, the use of any linker capable of stably and efficiently conjugating DLOS to an immunogenic carrier protein is contemplated. The use of linkers is well known in the conjugate vaccine field (see Dick et al., *Conjugate Vaccines*, J. M. Cruse and R. E. Lewis, Jr., eds., Karger, New York, pp. 48–114, the entire contents of which are hereby incorporated by reference).

dLOS may be directly covalently bonded to the carrier. This may be accomplished, for example, by using the cross linking reagent glutaraldehyde. However, in a preferred embodiment, dLOS and the carrier are separated by a linker. Presence of a linker promotes optimum immunogenicity of the conjugate and more efficient coupling of the dLOS with the carrier. Linkers separate the two antigenic components by chains whose length and flexibility can be adjusted as desired. Between the bifunctional sites, the chains can contain a variety of structural features, including heteroatoms and cleavage sites. Linkers also permit corresponding increases in tnanslational and rotational characteristics of the antigens, increasing access of the binding sites to soluble antibodies. Besides ADH, suitable linkers include, for example, heterodiflmctional linkers such as ϵ-aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention. Such compounds are discussed in detail by Dick et al., supra.

The presence of a carrier increases the immmunogenicity of the polysaccharide. In addition, antibodies raised against the carrier are medically beneficial. Polymeric immunogenic carriers can be a natural or synthetic material containing a primary and/or secondary amino group, an azido group or a carboxyl group. The carrier may be water soluble or insoluble.

Any one of a variety of immunogenic carrier proteins may be used in the conjugate vaccine of the present invention. Such classes of proteins include pili, outer membrane proteins and excreted toxins of pathogenic bacteria, nontoxic or "toxoid" forms of such excreted toxins, nontoxic proteins antigenically similar to bacterial toxins (cross-reacting materials or CRMs) and other proteins. Nonlimiting examples of bacterial toxoids contemplated for use in the present invention include tetanus toxin/toxoid, diphtheria toxin/toxoid, detoxified *P. aeruginosa* toxin A, cholera toxin/toxoid, pertussis toxin/toxoid and *Clostridium perfringens* exotoxins/toxoid. The toxoid forms of these bacterial toxins is preferred. The use of viral proteins (i.e. hepatitis B surface/core antigens; rotavirus VP 7 protein and respiratory syncytial virus F and G proteins) is also contemplated.

CRMs include $CRM_{197}$, antigenically equivalent to diphtheria toxin (Pappenheimer et al., *Immunochem.*, 9:891–906, 1972) and CRM3201, a genetically manipulated variant of pertussis toxin (Black et al., *Science*, 240:656–659, 1988). The use of immunogenic carrier proteins from non-mammalian sources including keyhole limpet hemocyanin, horseshoe crab hemocyanin and plant edestin is also within the scope of the invention.

There are many coupling methods which can be envisioned for dLOS-protein conjugates. In the examples set forth below, dLOS is selectively activated by 1-ethyl-3-(3-dimethylaminopropyl) carbodiimide (EDC)-mediated ADH derivatization of the terminal 3-deoxy-D-manno-2-octulosonic acid (KDO) group of dLOS, followed by EDC-mediated coupling to TT. Alternatively, another method for producing the instant conjugates involves cystamine derivatization of dLOS, by, for example, EDC-mediated derivatization, followed by disulfide conjugation to N-succimidyl-3-(2-pyridyldithio) propionate-derivatized protein. Other methods well known in the art for effecting conjugation of oligosaccharides to immunogenic carrier proteins are also within the scope of the invention. Such methods are described in, for example, U.S. Pat. Nos. 5,153,312 and 5,204,098; EP 0 497 525; and EP 0 245 045, the entire disclosures of which are hereby incorporated by reference.

The molar ratio of ADH to dLOS in the reaction mixture is typically between about 10:1 and about 250:1. A molar excess of ADH is used to ensure more efficient coupling and to limit dLOS-dLOS coupling. In a preferred embodiment, the molar ratio is between about 50:1 and about 150:1; in a most preferred embodiment, the molar ratio is about 100:1. Similar ratios of AH-dLOS to both TT and HMP in the reaction mixture are also contemplated. In a preferred embodiment, one ADH per dLOS is present in the AH-dLOS conjugate. In another preferred embodiment, in the final dLOS-carrier protein conjugate, the molar ratio of dLOS to carrier is between about 15 and about 75, preferably between about 25 and about 50.

Immunogenicity of the conjugates in both mice and rabbits is enhanced by the use of monophosphoryl lipid A plus trehalose dimycolate (Ribi-700; Ribi Immunochemical Research, Hamilton, Mont.) as an adjuvant. Although this adjuvant is not approved for use in humans, the skilled artisan will appreciate that other well known standard adjuvants may be used in the invention, including aluminum compounds (i.e. alum), chemically-modified lipopolysaccharide, suspensions of killed *Bordetella pertussis*, N-acetylmuramyl-L-alanyl-D-glutamine and other adjuvants known to one of ordinary skill in the art. The use of aluminum compounds is particularly preferred. Such adjuvants are described by Warren et al. (*Ann. Rev. Bioche.*, 4:369–388, 1986), the entire disclosure of which is hereby incorporated by reference.

The dLOS-carrier protein conjugates for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid maw likewise be used in the preparation of injectable preparations.

The conjugate vaccine of the invention may be in soluble or microparticular form, or may be incorporated into microspheres or microvesicles, including liposomes. Although various routes of vaccine administration including, for example, intramuscular, subcutaneous, intraperitoneal and intraarterial are contemplated, the preferred route is intramuscular administration. In a preferred embodiment, the dosage of the conjugate administered will range from about 10 µg to about 50 µg. In a more preferred embodiment, the amount administered will be between about 20 µg and about 40 µg. In a most preferred embodiment, the amount administered is about 25 µg. Greater doses may be administered on the basis of body weight. The exact dosage can be determined by routine dose/response protocols known to one of ordinary skill in the art.

The vaccine of the invention may be administered to warm-blooded mammals of any age and are adapted to induce active immunization in young mammals, particularly humans, against otitis media and respiratory infections caused by NTHi. As a childhood vaccine, the conjugate is administered at about 2 to 4 months of age. Typically, two booster injections of between about 10 µg and about 25 µg are administered at about 2 and again about 13 months after the initial injection. Alternatively, three booster injections are given at 2, 4 and 16 months after the initial injection.

The IgG antibodies elicited by systemic administration of the conjugate vaccine will transfer to local mucosa and inactivate NTHi inoculum on mucosal surfaces (i.e., nasal passages). Secretory IgA will also play a role in mucosal immunity if the conjugate vaccine is administered to the mucosa (i.e. intranasally). Thus, the conjugate vaccine will prevent local, as well as systemic, NTHi infection.

The examples describe conjugate vaccines using NTHi strains 9274 and 2019. Vaccines from other NTHi strains are within the scope of the present invention and are made using the same techniques. NTHi strains 9274 and 2019 are classified as types III and II, respectively. Other clinically relevant NTHi strains contemplated as sources of dLOS for generation of a dLOS-carrier conjugate vaccine include strains 1479, 5657 and 7502 (type I, IV and V, respectively). These strains, as well as strain 2019, are described by Campagnari et al. (*Infect Immun.*, 55:882–887, 1987) and Patrick et al. (*Infect Immun.*, 55:2902–2911, 1987), the entire contents of which are hereby incorporated by reference, and are generally available from the research community.

A multivalent vaccine comprising a mixture of conjugates, each having a dLOS from a different NTHi strain, is also within the scope of the invention. A person of ordinary skill in the art will appreciate that LOS from these other clinically relevant strains may be detoxified by removal of fatty acids therefrom as described in Example 2. In a preferred embodiment, the dLOS moieties thus obtained are at least about 5,000 fold less toxic than LOS itself. In a particularly preferred embodiment, the dLOSs are at least about 10,000 fold less toxic than dLOS. Determination of toxicity may be performed, for example, according to Example 8 below.

NTHi 9274 and 2019 were grown and LOS was isolated as described in the following example.

EXAMPLE 1

Bacterial Growth and LOS Purification

NTHi strain 9274 was isolated from middle ear fluids of a patient with otitis media and provided by Dr. M .A. Apicella (University of Iowa, Iowa City, Iowa). Also see Gu et al., *Infect. Immun.*, 63:4115–4120, 1995. NTHi strain 2019 was isolated from chronic bronchitis patients (Campagnari et al., supra.). Bacteria were grown on chocolate agar plates in a 5% $CO_2$ atmosphere at 37° C. for 8 hours, then transferred to 200 ml 3% brain-heart-infusion (BHI) medium (Difco, Detroit, Mich.) containing 5 µg/ml NAD and 2 µg/ml hemin (Sigma, St. Louis, Mo.). The medium was placed in an incubator shaker set at 150 rpm and 37° C. overnight. The culture broth was transferred to five 2.8 l flasks, each containing 1.4 liters BHI media Flasks were shaken at 140 rpm at 37° C. for 24 hours. The culture broth was centrifuged at 15,000×g for 30 minutes to separate cells and supernatant.

LOS was purified from cells by the classical phenol-water extraction method with modification (Westphal et al., *Meth. Carbohyd Chem.*, 5:83–91, 1965, incorporated by reference). Briefly, cells were grown overnight and treated with 90% phenol (45% final concentration) at 68–70° C. for 15–20 min., cooled on ice and centrifuged. After recovery of the upper aqueous phase, the remainder was re-extracted with water. Sodium acetate (5 mg/ml) was added to the combined aqueous phases and the LOS was precipitated with 2 volumes of acetone to reduce phospholipid contamination. The pellets were washed twice with 70% ethanol to reduce trace phenol, then dissolved in water. RNase and DNase were added (50–100 µg/ml) and samples were incubated at 37° C. for 3–5 hours. Proteinase K (0.5 mg/ml) was then added and the samples were incubated at 60° C. overnight, then centrifuged at least twice at 150,000×g for 3 hours. The gel-like LOS was dissolved in about 10 volumes of water and lyophilized.

LOS was also purified from the culture supernatant by gel filtration (Gu et al., *Anal. Biochem.*, 196:311–318, 1991, incorporated by reference). Briefly, 6–8 liters of culture supernatant were concentrated to 100–200 ml using a hollow-fiber cartridge with a 100,000 molecular weight cutoff (Amicon, Danvers, Mass.). To the concentrate was added 5–10 volumes of water, followed by reconcentration to about 400 ml. LOS containing outer membrane vesicles (OMV) were then pelleted by ultracentrifugation at 150,000×g and suspended in water to a 5–10% (v/v) suspension. To 10 ml of an opalescent OMV suspension, EDTA was added to a concentration of 2 mM, and the pH adjusted to 8.5 with 1 M NaOH. Sodium deoxycholate (Na-DOC) (2%, w/v) was added and the mixture was kept at 37° C. for 10 minutes to solubilize LOS from OMV. LOS was separated from outer membrane proteins on a 5×90 cm Sephacryl S-300 column (Pharmacia) using 20 mM Tris, pH 8.5, 2 mM EDTA, 1% Na-DOC, 0.02% sodium azide as an elution buffer. Proteins were monitored by absorbance at 280 nm.

LOS could be detected as ethanol precipitable materials as follows. To 200 µl aliquots of the column fractions, 3 volumes of ethanol (95%) were added after adjusting the aliquots to 0.25 M NaCl with 5 M NaCl. The mixtures were vortexed and LOS immediately precipitated. According to the LOS precipitation, the main LOS fractions were pooled, precipitated in 70% ethanol overnight as described above and collected by low speed centrifugation. LOS was dissolved in water to about 10 mg/ml for another cycle of ethanol precipitation to reduce residual NA-DOC, proteins and phospholipids, then washed with 70% ethanol, lyophilized and weighed.

The protein and nucleic acid content of purified LOS from both cells and culture supernatant was less than 1%.

The LOS purified from cells and from culture supernatant was combined and detoxified as described below.

EXAMPLE 2

Detoxification of LOS

LOS (160 mg), isolated as described in Example 1, was dried over phosphorus pentoxide ($P_2O_5$) for 3 days, suspended in 16 ml anhydrous hydrazine (Sigma) and incubated at 37° C. for 2 hours, mixing every 15 min. The solution was placed on ice, then added dropwise to cold acetone in an ice bath until a precipitate formed (≧90% acetone). The mixture was centrifuged at 5,000×g at 5° C. for 30 min. The pellet was washed twice with cold acetone, dissolved in pyrogen-free water to 20 mg/ml, and centrifuged at 150,000×g for 3 hours at 5° C. The supernatant was lyophilized and applied to a 1.6×90 cm SEPHADEX® G-50 gel filtration column (Pharmacia, Upssala, Sweden). The column was eluted with 25 mM ammonium acetate and monitored with a differential refractometer (R-400; Waters, Milford, Mass.). The eluate was assayed for carbohydrate content by the phenol-sulfuric acid method (Dubois et al., *Anal. Biochem.*, 28:250–256, 1956) and the carbohydrate fractions were pooled, lyophilized three times to remove the salt and designated dLOS.

After hydrazine treatment of LOS, the yield of dLOS ranged from 48% to 55% by weight for 9274 and 18% to 26% for 2019. Sodium dodecyl sulfate-polyacrylamide gel electrophoresis (SDS-PAGE) analysis of LOS and dLOS followed by silver staining showed that dLOS migrated faster than did LOS due to the removal of ester-linked fatty acids.

dLOS was derivatized with ADH as described in the following example.

EXAMPLE 3

Derivatization of dLOS

ADH was bound to the carboxyl group of the KDO moiety of dLOS to form AH-dLOS derivatives using EDC and N-hydroxysulfo-succinimide (sulfo-NHS) (Pierce, Rockford, Ill.). dLOS (70 mg) was dissolved in 7 ml 345 mM ADH (Aldrich, Milwaukee, Wis.) in water. The molar ratio of ADH to dLOS was about 100 to 1. Solid sulfo-NHS was added to a final concentration of 8 mM. The pH was adjusted to 4.8 with 1 M HCl and EDC was added to a concentration of 0.1 M. The reaction mixture was stirred and maintained at pH 4.8±0.2 with 1 M HCl for three hours at room temperature. The reaction mixture was adjusted to pH 7.0 and applied to the G-50 column.

The eluate containing AH-dLOS was assayed for carbohydrate (dLOS) content using dLOS as a standard, then calculated as moles using a molecular weight of 3,000. The amount of AH in AH-dLOS was measured by a modified TNBS method using ADH as a standard and measuring absorbance at $OD_{490nm}$ (Kemp et al., *J. Immunol. Meth.*, 94:65–72, 1986).

The peaks containing both carbohydrate and AH were pooled, lyophilized three times to remove the salt, and designated as AH-dLOS. AH-dLOS was measured for its composition using dLOS and ADH as standards. The final molar ratio of AH to dLOS in the AH-dLOS product=moles of AH/moles of dLOS. For strain 9274, the molar ratio of AH to dLOS was 0.47 and 0.55, indicating that about 50% of the LOS was derivatized. For strain 2019, the molar ratio of AH to dLOS was 0.37. The yields for strain 9274, on the basis of carbohydrate content, were 43% and 52% for the two lots of AH-dLOS. For strain 2019, the yield was 94%.

AH-dLOS was conjugated to TT as described in the following example.

EXAMPLE 4

Conjugation of AH-dLOS to Carrier Proteins

AH-dLOS was coupled to carboxyl groups on TT (strains 9274 and 2019) or HMPs (Strain 9274) at pH 5.6 with EDC.

HMPs were purified from NTHI strain 12 as described by Barenkamp et al. (*Infect. Immun.*, 64:1246–1251, 1996). AH-LOS (20 mg) was dissolved in 2 ml distilled water and mixed with 10 mg TT (5.9 mg/ml) (Connaught Labs, Inc., Swiftwater, Pa.) or 8 mg HMP (4 mg/ml). The molar ratio of AH-dLOS to TT and HMP was about 100 to 1. The pH was adjusted to 5.6 with 0.1 M HCl, followed by addition of EDC to a concentration of 0.1 M. The reaction mixture was stirred and maintained at pH 5.6 i 0.2 with 0.1 M HCl for 1 to 3 hours at room temperature. The reaction mixture was adjusted to pH 7.0, centrifuged at 1,000×g for 10 min and purified using a 1.6×90 cm SEPHACRYL® S-300 gel filtration column (Pharmacia) equilibrated with 0.9% NaCl. The eluate was monitored for protein by determining $OD_{280}$ of the column fractions and assayed for carbohydrate content. Column fractions containing both protein and carbohydrate were pooled and designated as dLOS-TT or dLOS-HMP. Both conjugates were analyzed for carbohydrate and protein using dLOS and BSA as standards. For strain 9274, the molar ratio of dLOS to TT in the two lots of conjugate preparations was 26:1 and 50:1 and the yield was 10 to 15% (Table 1). For strain 2019, the molar ratio of dLOS to TT in the two lots of conjugate preparations was 31:1 and 42:1 and the yield was 18 to 26%.

TABLE 1A

Composition and yield of NTHi 9274 conjugates

| Conjugate | dLOS (μg/ml) | protein (μg/ml) | Ratio of dLOS to protein[a] (mol of dLOS/ mol of protein) | Yield[b] (%) | $A_{405}$ (hyper- immune serum/MAb) |
|---|---|---|---|---|---|
| dLOS-TT1 | 100 | 190 | 26 | 15 | 1.56/1.49 |
| dLOS-TT2 | 90 | 90 | 50 | 11 | 1.50/1.38 |
| dLOS-HMP | 235 | 274 | 34 | 15 | 1.53/1.45 |

[a]The ratio is expressed as moles of dLOS per mole of protein using molecular weight of 3,000 for dLOS, 150,000 for TT, and 120,000 for HMP.
[b]Based on the starting amounts of dLOS and dLOS contained in the conjugates.
[c]The antigenicity of conjugates was expressed as ELISA reactivity at $A_{405}$ when the conjugates were used as coating antigens (10 μg/ml) and the mouse hyperimmune sera (1/500) and MAb 6245B4 (1/1000) were used as binding antibodies. LOS (10 μg/ml) also showed $A_{405}$ values of 1.02 and 1.10 under the same conditions.

TABLE 1B

Composition, yield and antigenicity of NTHi 2019 conjugates

| Conjugate | Amt (μg/ml) of:[a] dLOS | TT | Molar ratio[b] dLOS to TT | Yield (%) | $A_{405}$[c] (hyperimmune serum) |
|---|---|---|---|---|---|
| dLOS-TT1 | 238 | 380 | 31 | 18 | 1.4 |
| dLOS-TT2 | 280 | 340 | 42 | 26 | 1.2 |

[a]The ratio is expressed as moles of dLOS per mole of protein with molecular weights of 3,000 for dLOS and 150,000 for TT.
[b]Based on the starting amount of dLOS and the dLOS contained in the conjugates as measured by the phenol-sulfuric acid method.
[c]The antigenicity of conjugates was expressed as ELISA reactivity at $A_{405}$ when the conjugates were used as coating antigens (10 μg/ml) and a rabbit hyperimmune serum (1/4,000) was used as a binding antibody. LOS (10 μg/ml) also showed an $A_{405}$ value of 1.7 under the same conditions.

The antigenicity of the conjugates was determined as described below.

EXAMPLE 5

Antienicity of dLOS, AH-dLOS and dLOS-TT

The antigenicity of dLOS, AH-dLOS and the dLOS conjugates was tested by double immunodiffusion and/or enzyme-linked immunosorbent assay (ELISA) using hyperimmune serum to NTHi 9274 or 2019 whole cells and a mouse monoclonal antibody (6245B4) generated against NTHi 9274 LOS. Hyperimmune serum was produced by intraperitoneally injecting 10 Balb/c mice three times at two week intervals with about $10^9$ bacteria per injection. Blood samples were collected one week after the third injection.

Double immunodiffusion was performed in 0.8% agarose in phosphate-buffered saline (PBS, pH 7.4). Both AH-dLOS and the dLOS conjugates bound to the LOS MAb. dLOS-TT and LOS formed identical precipitation lines in double immunodiffusion. Both showed comparable binding to the LOS MAb and hyperimmune sera by ELISA, indicating that dLOS retained the LOS antigenicity. dLOS-HMP exhibited similar results to those of dLOS-TT.

For ELISA, a 100 μl sample of conjugates at 10 μg dLOS/ml in PBS, or LOS at 10 μg/ml in PBS containing 10 mM $MgCl_2$ was used to coat microwell plates overnight (Immuno I plate; Dynatech Laboratories, Inc., Alexandria, Va.). The plate was blocked with 150 μl 1% BSA in PBS for 1 hour, followed by addition of 100 μl diluted mouse serum or MAb and incubation for 3 hours. Alkaline phosphatase-conjugated goat anti-mouse IgG or IgM (Sigma) was then added followed by incubation for an additional 2 hours. Diluents for sera and phosphatase were 1% BSA in PBS containing 0.05% Tween-20 (pH 7.4). All steps were performed at room temperature and, between each step, the wells were washed five times with 0.9% NaCl containing 0.05% Tween-20 (pH 7.4). The enzyme substrate was added and the plates were read with a microplate autoreader set at $OD_{405nm}$ (EL309, Bio-tek Instruments). The conjugates showed an ELISA binding reactivity comparable to that of LOS with both LOS MAb and immune sera to whole NTHi 9274 or 2019 cells.

The immunogenicity of the NTHi 9274 dLOS-TT conjugates was determined as described in the following example.

EXAMPLE 6

Immunogenicity of NTHi 9274 dLOS-TT Conjugates

The immunogenicity of the NTHi 9274 dLOS-TT conjugates was tested in both mice and rabbits. Five week old general purpose mice (NIH/Swiss, female), ten mice per group, were subcutaneously immunized with 5 μg of the conjugates (based on carbohydrate weight), LOS, dLOS, dLOS plus TT (10 μg) or TT only in 0.2 ml 0.9% NaCl with or without Ribi-700 adjuvant containing 50 μg monophosphoryl lipid A and 50 μg synthetic trehalose dimycolate. Mice were injected three times at three week intervals and bled 14 days after the first injection and seven days after the second and third injections.

New Zealand white rabbits (female, 2–3 kg), 2–3 rabbits per group, were subcutaneously immunized with 50 μg dLOS or conjugates (carbohydrate weight) in 1 ml 0.9% NaCi with or without Ribi-700 adjuvant. Rabbits were injected twice at one-month intervals and bled two weeks after the first injection and 11–14 days after the second injection.

Serum anti-LOS levels were expressed in ELISA units, using NTHi 9274 LOS as a coating antigen and the NTHI 9274 hyperimmune serum as a reference assigned values of 4,000 and 3,500 units/ml for IgG and IgM, respectively. Pre-sera contained five (3–9) units of IgG and three (1–6) units of IgM. Serum TT antibody was measured by ELISA in which TT (5 μg/ml) was used as a coating antigen and a horse anti-TT serum (20 IU/ml) as a reference assigned a value of 320 ELISA units/ml for IgG and IgM, respectively. Serum HMP antibody was measured by ELISA in which HMP (5 μg/ml) was used as a coating antigen, and expressed as ELISA units on the basis of a reference mouse serum produced by three injections of HMP and assigned values of 2,000 and 10 ELISA units/ml for IgG and IgM, respectively.

Antibody levels are expressed as the geometric mean in ELISA units of n independent observations ±standard deviation or range (n<4). Significance was tested with the two-sided T-test and P values <0.05 were considered significant.

In mice, dLOS or a mixture of dLOS and TT (unconjugated) did not elicit LOS antibodies. The antibody response to LOS elicited by the conjugates is summarized in Table 2. dLOS-TT elicited low LOS IgG levels after the first injection which increased 28 to 162-fold after the second and third injections (P<0.01). dLOS-HMP elicited significant IgG levels after the first injection which also increased after the second and third injections (104 to 486-fold, P<0.01). After 3 injections, dLOS-HMP elicited higher IgG levels than did dLOS-TT1 (P<0.01) or dLOS-TT2 (P<0.05). LOS alone elicited low IgG levels after the first injection which increased 25 to 84-fold after the second and third injections (P<0.05).

The immunogenicity of the conjugates was significantly enhanced by Ribi adjuvant. One dose elicited comparable or higher IgG levels than did two doses of the conjugates alone. After three injections, about a five-fold increase in IgG was observed after three injections (P<0.01).

The conjugates elicited low to medium levels of IgM after each injection. LOS elicited high IgM levels after the first injection which increased after the second and third injections (P<0.01). Ribi adjuvant enhanced IgM levels in the conjugate groups.

As used in all tables set forth herein, "adjuvant" is Ribi-700 adjuvant.

TABLE 2

Murine antibody response to NTHi 9274 LOS elicited by conjugates

| Immunogen | Injection No. | Geometric mean ± SD ELISA units | |
|---|---|---|---|
| | | IgG | IgM |
| dLOS | 1 | 5 (3–9) | 5 (3–8) |
| | 2 | 6 (3–10) | 3 (1–5) |
| | 3 | 4 (3–7) | 2 (1–3) |
| dLOS-TT1 | 1 | 8 (5–13) +[a] | 14 (8–25) |
| | 2 | 140 (55–352)++ | 42 (7–237) |
| | 3 | 217 (91–516) | 52 (11–251) |
| dLOS-TT2 | 1 | 10 (3–36)+ | 17 (4–84) |
| | 2 | 217 (47–1,007)++ | 42 (7–237) |
| | 3 | 810 (229–2,890) | 42 (24–74) |
| dLOS-TT2 + adjuvant | 1 | 270 (62–1,168)**[a] | 470 (266–828) |
| | 2 | 1,257 (313–5,045)** | 101 (64–160) |
| | 3 | 4,698 (2,664–8,284) | 81 (39–169) |
| dLOS-HMP | 1 | 72 (45–115)+ | 11 (7–18) |
| | 2 | 522 (296–920)++ | 101 (64–160) |
| | 3 | 2,430 (1,168–5,055) | 14 (8–25) |
| dLOS-HMP + adjuvant | 1 | 1,403 (780–2,524)+ | 243 (91–516) |
| | 2 | 7,290 (2,252–23,593)++ | 421 (234–757) |
| | 3 | 11,006 (6,233–19,435) | 19 (11–33) |
| dLOS + TT | 1 | 4 (3–7) | 2 (2–4) |
| | 2 | 4 (3–5) | 3 (1–6) |
| | 3 | 4 (3–7) | 3 (1–11) |
| LOS | 1 | 65 (38–110)* | 195 (123–310) |
| | 2 | 125 (60–263)** | 338 (161–709) |
| | 3 | 419 (238–739) | 470 (186–1,186) |

[a] * versus **, P < 0.05 and + versus ++, P < 0.01.

The murine antibody response to TT elicited by the conjugates is shown in Table 3. dLOS did not elicit antibodies to TT. However, both lots of dLOS-TT elicited IgG antibodies to TT after the first injection which rose significantly after the second and third injections (P<0.01). Either TT alone, or the mixture of TT and dLOS resulted in enhanced IgG resonses after two or three injections compared to the conjugates (P<0.01 or <0.05). Ribi adjuvant enhanced the levels of IgG in the conjugate groups.

The conjugates, TT or the unconjugated mixture of TT and dLOS elicited low IgM levels after each injection. Ribi adjuvant enhanced the levels of IgM in the conjugate groups.

TABLE 3

Murine antibody response to tetanus toxoid elicited by dLOS-TT conjugates

| Immunogen | Injection No. | Geometric mean ± SD ELISA units | |
|---|---|---|---|
| | | IgG | IgM |
| dLOS | 1 | <1 | <3 |
| | 2 | <1 | <3 |
| | 3 | <1 | <3 |
| dLOS-TT1 | 1 | 30 (14–62)** | 16 (9–27) |
| | 2 | 112 (29–433)** | 37 (12–116) |
| | 3 | 419 (238–739) | 12 (8–20) |
| dLOS-TT2 | 1 | 8 (3–25)+[a] | 12 (8–20) |
| | 2 | 90 (17–463)++ | 19 (8–49) |
| | 3 | 522 (296–920) | 4 (3–7) |
| dLOS-TT2 + adjuvant | 1 | 72 (13–397)+ | 30 (14–50) |
| | 2 | 1,257 (713–2,217)++ | 72 (45–115) |
| | 3 | 1,257 (713–2,217) | 112 (71–178) |
| dLOS + TT | 1 | 37 (24–59)+ | 4 (3–7) |
| | 2 | 1,257 (713–2,217)++ | 12 (8–20) |
| | 3 | 2,430 (863–6,846) | 19 (8–49) |
| TT | 1 | 24 (15–38)+ | 4 (3–7) |
| | 2 | 650 (409–1,033)++ | 12 (5–30) |
| | 3 | 1,951 (505–7,528) | 19 (4–93) |

[a] * versus **, P < 0.05 and + versus ++, P < 0.01.

dLOS itself did not elicit anti-HMP antibodies. dLOS-HMP elicited low IgG levels after the first injection which rose significantly after the second and third injections (P<0.01). HMP alone showed similar results to dLOS-HMP and no significant differences in IgG levels between the two groups were observed after 3 injections (P>0.05). IgG levels were significantly increased by inclusion of adjuvant in the conjugate group (P<0.01). dLOS-HMP or HMP alone elicited low IgM levels after each injection. Ribi adjuvant enhanced IgM levels elicited by dLOS-HMP which increased significantly after each injection (P<0.01). The results are summarized in Table 4.

TABLE 4

Murine antibody response to high molecular weight proteins of NTHi elicited by dLOS-HMP conjugates

| Immunogen | Injection No. | Geometric mean ± SD ELISA units | |
|---|---|---|---|
| | | IgG | IgM |
| dLOS | 1 | <1 | <3 |
| | 2 | <1 | <3 |
| | 3 | <1 | <3 |
| dLOS-HMP | 1 | 2 (1–3)+[a] | 6 (3–12) |
| | 2 | 243 (117–506)++ | 12 (8–20) |
| | 3 | 1,756 (732–4,134) | 8 (3–19) |
| dLOS-HMP + adjuvant | 1 | 243 (123–490) | 5 (3–10) |
| | 2 | 2,187 (1,096–4,365) | 52 (29–93) |
| | 3 | >6,561 | 130 (74–229) |

TABLE 4-continued

Murine antibody response to high molecular weight proteins of NTHi elicited by dLOS-HMP conjugates

| Immunogen | Injection No. | Geometric mean ± SD ELISA units | |
|---|---|---|---|
| | | IgG | IgM |
| HMP | 1 | 1 | 3 |
| | 2 | 729 (205–2,592) | 5 (3–10) |
| | 3 | 1,516 (860–2,674) | 7 (4–12) |

[a] + versus ++, P < 0.01.

Two to three rabbits for each group were subcutaneously immunized on days 0 and 28 with 50 μg dLOS, conjugates or conjugates plus Ribi adjuvant. Blood samples were collected on days 0, 14 and 38–42. dLOS itself did not elicit anti-LOS antibodies in rabbits. dLOS-TT elicited a significant increase in IgG levels after the first and second injections (39 to 168-fold, P<0.01). The results for dLOS-HMP were similar to those observed for dLOS-TT (27 to 243-fold). Ribi adjuvant enhanced IgG levels elicited by dLOS-TT (P<0.05), but not by dLOS-HMP, after the second injections. Both conjugates, either alone or with adjuvant, elicited low IgM levels after each injection. Pre-sera contained 1 unit for IgG and <1 unit for IgM. The results are summarized in Table 5.

TABLE 5

Rabbit antibody response to NTHi 9274 LOS elicited by conjugates

| Immunogen | Injection No. | Geometric mean (range) ELISA units | |
|---|---|---|---|
| | | IgG | IgM |
| dLOS | 1 | 1 | <1 |
| | 2 | 1 | <1 |
| dLOS-TT | 1 | 39 (27–81)*[a] | 9 |
| | 2 | 168 (81–243)** | 9 |
| dLOS-TT + adjuvant | 1 | 27 | 5 (3–9) |
| | 2 | 421 (243–729)++[a] | 16 (9–27) |
| dLOS-HMP | 1 | 27 | 3 |
| | 2 | 243 | 9 |
| dLOS-HMP + adjuvant | 1 | 81 | 9 |
| | 2 | 243 | 9 |

[a] * versus **, P < 0.05 and + versus ++, P < 0.01.

dLOS itself did not elicit TT antibodies in rabbits. dLOS-TT elicited anti-TT IgG after the first injection which rose significantly after the second injection. IgG levels were enhanced by adjuvant 3-fold after the second injection. Both conjugates, either alone or with adjuvant, elicited low IgM levels after each injection. The results are summarized in Table 6.

TABLE 6

Rabbit antibody response to tetanus toxoid elicited by dLOS-TT conjugates

| Immunogen | Injection No. | Geometric mean (range) ELISA units | |
|---|---|---|---|
| | | IgG | IgM |
| dLOS | 1 | <3 | 1 |
| | 2 | <3 | 1 |
| dLOS-TT | 1 | 19 (9–27) | 9 |
| | 2 | 729 | 13 (9–27) |

TABLE 6-continued

Rabbit antibody response to tetanus toxoid elicited by dLOS-TT conjugates

| Immunogen | Injection No. | Geometric mean (range) ELISA units | |
|---|---|---|---|
| | | IgG | IgM |
| dLOS-TT2 + adjuvant | 1 | 16 (9–27) | 3 |
| | 2 | 2,187 | 5 (3–9) | dLOS itself did not elicit HMP antibodies in rabbits. dLOS-HMP elicited anti-HMP IgG after the first injection which rose significantly after the second injection. IgG levels were enhanced by adjuvant 3-fold after the second injection. Both conjugates, either alone or with adjuvant, elicited low IgM levels after each injection. The results are summarzed in Table 7.

TABLE 7

Rabbit antibody response to high molecular weight proteins elicited by dLOS-HMP conjugates

| Immunogen | Injection No. | Geometric mean (range) ELISA units | |
|---|---|---|---|
| | | IgG | IgM |
| dLOS | 1 | <3 | 1 |
| | 2 | <3 | 1 |
| dLOS-HMP | 1 | 16 (9–27)+[a] | 3 |
| | 2 | 421 (243–729)++ | 3 |
| dLOS-HMP + adjuvant | 1 | 27 | 3 |
| | 2 | 1,263 (729–2,187)+++ | 3 |

[a] + versus ++, P < 0.01 and ++ versus +++, P = 0.0519.

EXAMPLE 7

Immunoenicity of NTHi 2019 dLOS-TT Conjugates

Serum anti-LOS levels were expressed in ELISA units, using NTH 2019 LOS as a coating antigen and the NTHi 2019 hyperimmune serum as a reference assigned values of 4,000 and 3,500 units/ml for IgG and IgM, respectively. Pre-sera contained five (3–9) units of IgG and three (1–6) units of IgM. Serum TT antibody was measured by ELISA in which TT (5 μg/ml) was used as a coating antigen and a horse anti-TT serum (20 IU/ml) as a reference assigned a value of 320 ELISA units/ml for IgG and IgM, respectively.

Antibody levels are expressed as the geometric mean in ELISA units of n independent observations ±standard deviation or range (n<4). Significance was tested with the two-sided T-test and P values <0.05 were considered significant.

The immunogenicity of the NTHi 2019 dLOS-TT conjugates was tested in both rabbits and mice. New Zealand white rabbits (female, 2–3 kg), 1–3 rabbits per group, were subcutaneously and intramuscularly immunized with 50 μg dLOS, dLOS-TT$_1$, dLOS-TT$_1$ with Ribi adjuvant or LOS (carbohydrate weight) in 1 ml 0.9% NaCl. Rabbits were injected three times at one-month intervals and bled 0 and 10–14 days after the first, second and third injections; 1, 3, and 6 months after the third injection; and 10 days after the fourth injection.

dLOS itself did not elicit anti-LOS antibodies in rabbits. dLOS-TT elicited a significant increase in IgG levels after the second and third injections (40 to 58-fold, P<0.01). Ribi adjuvant significantly enhanced IgG levels elicited by dLOS-TT (P<0.05) after the second injection. Pre-sera contained 1 unit for IgG and <1 unit for IgM. The results are summarized in Table 8.

TABLE 8

Rabbit antibody response to NTHi 2019 LOS elicited by dLOS-TT

| Immunogen units[a] | Bleeding no.[b] | IgG Geometric mean (range) ELISA units |
|---|---|---|
| dLOS | 1 | 3 |
| | 2 | 3 |
| | 3 | 3 |
| | 4 | 3 |
| dLOS-TT1 | 1 | 1.4 (1–3) |
| | 2 | 3 |
| | 3 | 56 (27–81) |
| | 4 | 81 (27–243) |
| | 5 | 39 (27–81) |
| | 6 | 19 (9–27) |
| | 7 | 9 |
| | 8 | 81 |
| dLOS-TT1 + adjuvant | 1 | 1 |
| | 2 | 16 (9–27) |
| | 3 | 729 |
| | 4 | 1,263 (729–2187) |
| | 5 | 729 |
| | 6 | 421 (243–729) |
| | 7 | 243 (81–729) |
| | 8 | 1,263 |
| LOS | 1 | 3 |
| | 2 | 3 |
| | 3 | 3 |
| | 4 | 3 |

[a]One to three rabbits for each group were subcutaneously and intramuscularly immunized on 0, 1, 2, and 6 months with 5 ug of dLOS, dLOS-TT, dLOS-TT with Ribi adjuvant, or LOS.
[b]Blood samples were collected on 0, 10–14 days after the 1st, 2nd, and 3rd injection (2–4), 1, 3, and 6 months after the 3rd injection (5–7), and 10 days after the 4th injection (8).

dLOS itself did not elicit TT antibodies in rabbits. dLOS-TT elicited anti-TT IgG after the first injection which rose significantly after the second injection. IgG levels were enhanced by adjuvant 3-fold after the second injection. The results are sumarized in Table 9.

TABLE 9

Rabbit antibody response to TT elicited by dLOS-TT from NTHi 2019

| Immunogen units[a] | Bleeding no.[b] | IgG Geometric mean (range) ELISA units |
|---|---|---|
| dLOS (or LOS) | 1 | 1 |
| | 2 | 1 |
| | 3 | 1 |
| | 4 | 1 |
| dLOS-TT1 | 1 | 1.4 (1–3) |
| | 2 | 8 (5–10) |
| | 3 | 810 |
| | 4 | 1,168 (810–2,430) |
| | 5 | 810 |
| | 6 | 270 |
| | 7 | 130 (90–270) |
| | 8 | 810 |
| dLOS-TT1 + adjuvant | 1 | 1 |
| | 2 | 30 |
| | 3 | 2,430 |
| | 4 | 4,209 (2,430–7,290) |
| | 5 | 1,403 (810–2,430) |
| | 6 | 468 (270–810) |
| | 7 | 156 (90–270) |
| | 8 | 4,209 |

[a], [b]: See Table 8.

Female Balb/c mice (10–20 mice per group), were subcutaneously immunized with 5 μg (based on carbohydrate weight) of dLOS, dLOS-TT$_1$, dLOS-TT with Ribi adjuvant or LOS in 0.2 ml 0.9% NaCl. Mice were injected three times at three week intervals and bled 14 days after the first injection, seven days after the second and third injections and 1 week, 1 month and 5 months after the third injection.

dLOS-TT did not elicit antibodies against dLOS, and elicited a weak antibody response against LOS. Immunogenicity of the conjugate was increased four fold after the first injection and 14 fold after the second injection. The response was not greatly enhanced by adjuvant after the first and second injections; however, higher levels of IgG were maintained after injections 3, 4, and 5 in the presence of adjuvant. The results are summarized in Table 10.

TABLE 10

Murine antibody response to NTHi 2019 LOS elicited by dLOS-TT

| Immunogen[a] | Bleeding no.[b] | IgG Geometric mean (± SD range) ELISA units |
|---|---|---|
| dLOS | 1 | 4 (2–8) |
| | 2 | 3 |
| | 3 | 3 |
| dLOS-TT1 | 1 | 11 (7–18) |
| | 2 | 42 (12–147) |
| | 3 | 157 (86–286) |
| | 4 | 52 (12–228) |
| | 5 | 14 (8–25) |
| dLOS-TT1 + adjuvant | 1 | 6 (2–16) |
| | 2 | 42 (16–112) |
| | 3 | 101 (24–423) |
| | 4 | 101 (20–515) |
| | 5 | 157 (45–548) |
| LOS | 1 | 6 (3–12) |
| | 2 | 9 |
| | 3 | 9 |

[a]Ten to twenty mice for each group were given a total of three subcutaneous injections at 3-week intervals with 5 ug of dLOS, dLOS-TT, dLOS-TT with Ribi adjuvant, or LOS.
[b]Blood samples were collected 2 weeks after the 1st injection, 1 week after the 2nd injection, and 1 week, 1 month, and 5 months after the 3rd injection (3–5).

To determine the residual endotoxin reactivity of dLOS, both the limulus amebocyte lysate (LAL) assay and mouse lethal toxicity assays were used as described in the following two examples.

EXAMPLE 8

Lirnulus Amebocyte Assay and Rabbit Pyrogen Test

LOS, dLOS and dLOS conjugates were diluted with pyrogen-free water. Equal volumes (100 μl) of samples and Limulus amebocyte lysate were mixed and incubated at 37° C. for 1 hour. Gelation of the lysate at the minimal LOS concentration was determined by inverting the mixture. A firm gel was considered a positive reaction (Hochstein et al., *Bull. Parenteral Drug Assoc.*, 27:139–148, 1973). All reagents were from the U.S. Food and Drug Administration, Bethesda, Md. The sensitivity of the LAL assay is 0.09 EU per ml. By the LAL assay, the LOS from strain 9274 had the LAL reactivity at 10,000 EU/μg, while the dLOS exhibited this reactivity at 1 EU/μg. Thus, dLOS was 10,000 fold less active than untreated LOS in promoting LAL gelation. For the LOS from strain 2019, the LAL reactivity was 10,000 EU/μg, while the dLOS exhibited this reeactivity at 0.5 EU/μg. This represents a 2×10,000-fold reduction in toxicity of dLOS compared to LOS.

Pyrogenicity of the strain 9274 dLOS-TT conjugate in rabbits was assayed by H. D. Hochstein, U.S. FDA. dLOS-TT conjugate (25 μg) was intravenously injected into each rabbit, assuming this is one dose for human use. The conjugate was not pyrogenic in rabbits when injected at 8–9 μg/kg of rabbit body weight. In comparison, the World Health Organization (WHO) specification for Hib polysaccharide conjugate vaccines is to be nonpyrogenic at 1 μg/kg of rabbit body weight. The conjugates were also assayed for general safety by H. D. Hochstein and were deemed acceptable by the requirements of 21 C.F.R § 610.11.

EXAMPLE 9

Mouse Lethal Toxicity Test

LOS and dLOS from strain 9274 were tested by a mouse lethality assay (Galanos et al., *Proc. Natl. Acad. Sci. USA*, 76:5939–5943, 1979). Briefly, female seven week old inbred BALB/c mice, 8 per group, were injected intraperitoneally with 8 mg D-galactosamine HCl (Sigma) dissolved in 0.2 ml pyrogen-free water (400 mg/kg). Within 30 min., the animals were given different amounts of the experimental preparations in 0.2 ml water by intravenous route. Lethality was observed over a four day period and the $LD_{50}$ was calculated.

The $LD_{50}$ of dLOS was 18.3 μg, while the $LD_{50}$ of LOS was 0.3 ng. Thus, dLOS was at least 10,000 fold less toxic than untreated LOS.

EXAMPLE 10

Bactericidal Assay of dLOS-TT Rabbit Antisera

Bactericidal activity of dLOS-TT antisera was based on a modification of a microbactericidal assay (Frasch et al., *J. Exp. Med.*, 147:629–644, 1978; Jennings et al., *J. Exp. Med.*, 165:1207–1221, 1987), the entire contents of which are hereby incorporated by reference. Rabbit preimmune and postimmune sera obtained after two injections of conjugate were inactivated at 56° C. for 30 min. and tested for bactericidal activity against NTHi strain 9274, the prototype strain 3198 (Type III) and strain NTHi 2019. Briefly, serial twofold dilutions of the sera were made in Dulbecco's PBS containing calcium, magnesium, and 0.1% gelatin (DPBSG), such that 50 μl sera or diluted sera were present in each well of a sterile 96-well plate. NTHi strains were grown on chocolate agar plates at 37° C., 5% $CO_2$ overnight and 3–5 colonies were transferred to another plate and incubated for 4.5 hours. Bacteria were diluted in DPBSG, and 30 μl bacterial suspension (about $3 \times 10^3$ CFU/ml) were added to each well. Infant rabbit serum (15 μl/well) was added as a source of complement (Pel-Freez, Brown Deer, Wis.) for strains 9274 and 3198. Guinea pig serum (Sigma) was used as a source of complement for strain 2019. Plates were incubated at 37° C. for 30 min. Fifty μl of the mixture was removed from each well and spread on chocolate agar plates (100×15 mm) which were then incubated at 37° C., 5% $CO_2$ overnight and colonies were counted. Controls included complement, inactive complement and a positive serum. The results are shown in Tables 11 (NTHi 9274) and 12 (NTHi 2019).

TABLE 11

Bactericidal activity of NTHi 9274 dLOS and dLOS conjugates

| Rabbit No. | Immunogen | Bactericidal titer | | Geometric Mean Titer + SD | |
|---|---|---|---|---|---|
| | | pre- | post-sera | pre- | post-sera |
| 1136 | dLOS | 2 | 2 | 2 | 2 |
| 1135 | dLOS-TT | 4 | 64 | | |
| 104 | dLOS-TT | 0 | 32 | 1 | 51 (35–76) |
| 108 | dLOS-TT | 0 | 64 | | |
| 1139 | dLOS-TT + Ribi | 0 | 32 | 2 | 64 (24–171) |
| 105 | dLOS-TT + Ribi | 4 | 128 | | |
| 1 | dLOS-HMP | 8 | 128 | 4 | 64 (24–171) |
| 2 | dLOS-HMP | 2 | 32 | | |
| 3 | dLOS-HMP + Ribi | 2 | 64 | 2 | 64 |

TABLE 12

Bactericidal activity of NTHi 2019 dLOS and dLOS conjugates

| Immunogen[a] | Rabbit number[b] | Bactericidal titer[c] |
|---|---|---|
| dLOS | 2005 | <2 |
| dLOS-TT | 110 | <2 |
| | 113 | 2 |
| | 1137 | <2 |
| dLOS-TT + adjuvant | 1131 | 2 |
| | 1132 | 8 |
| LOS | 2004 | <2 |

[a]See Table 8, footnote.
[b]Pre- and postimmune sera obtained after three injections were used.
[c]Expressed as the fold increase above the value for preimmune sera and given as the reciprocal of the serum dilution causing > 50% killing of the bacteria.

Figure 1:
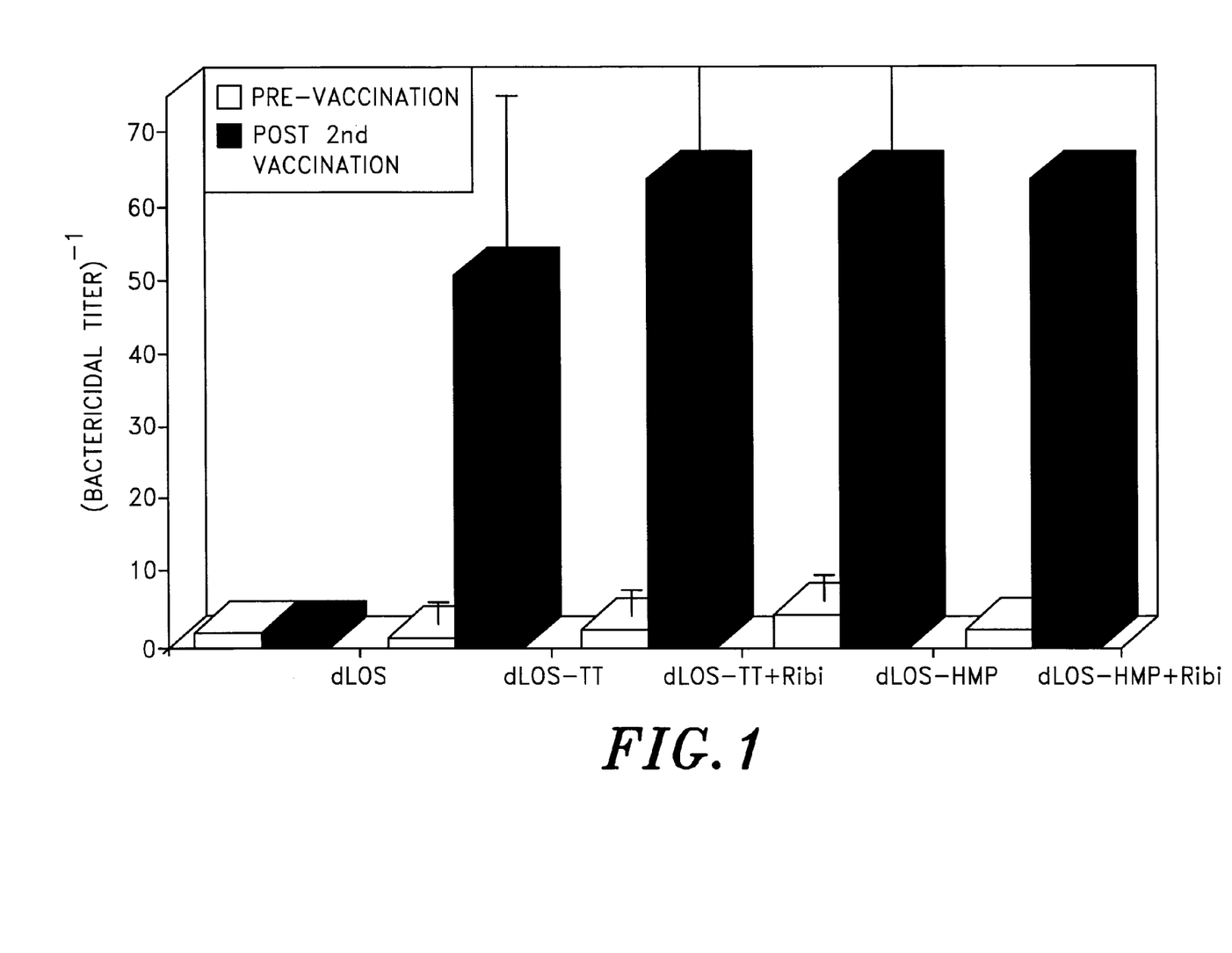
FIG. 1 shows the bactericidal activity of rabbit immune serum generated against dLOS, dLOS-TT, dLOS-TT plus adjuvant, dLOS-HMP and dLOS-HMP plus adjuvant. The y-axis shows the reciprocal of bactericidal titer. The reciprocal of bactericidal titer is proportional to bactericidal activity.

The highest serum dilution causing a >50% killing was expressed as the reciprocal bactericidal titer. The immune sera in the presence or absence of adjuvant exhibited bactericidal activity against NTHi strain 9274 with mean titers of 1:51 and 1:64 (FIG. 1). There was a positive correlation between LOS IgG antibody levels and bactericidal titers (r=0.81, P<0.01). The immune sera also exhibited bactericidal activity against the LOS prototype strain 3198 (type III) with titers ranging from 1:2 to 1:16.

EXAMPLE 11

Binding Reactivities of dLOS-TT to NmHi Clinical Isolates

The reactivities of rabbit immune sera elicited by the dLOS-TT conjugates from NTHi 9274 and 2019 were analyzed by a whole cell ELISA using 155 NTHi clinical isolate stains. By whole cell ELISA, rabbit sera elicited by dLOS-TT conjugates from strain 9274 showed binding reactivities to 60–81% of U.S. strains and 45–80% of Japanese strains. Rabbit sera elicited by conjugates from strain 2019 showed binding reactivities to 21–57% of U.S. strains and 20–55% of Japanese strains. Combined sera elicited by strains 9274 and 2019 showed binding reactivities to 78–86% of U.S. strains and 75–93% of Japanese strains. The results are summarized in Table 13.

TABLE 13

Binding reactivities of rabbit immunosera elicited by conjugates from NTHi strains 9274 and 2019

| Immunosera | ELISA binding reactivities using 155 clinical isolates % (P/T) | |
|---|---|---|
| | USA | Japan |
| 1. dLOS-TT (9274) | 81 (81/100) | 80 (44/55) |
| 2. dLOS-TT (9274) + adjuvant | 60 (60/100) | 60 (33/55) |
| 3. dLOS-HMP (9274) | 60 (60/100) | 45 (25/55) |
| 4. dLOS-HMP (9274) + adjuvant | 62 (62/100) | 45 (25/55) |
| 5. dLOS-TT (2019) | 57 (57/100) | 55 (30/55) |
| 6. dLOS-TT (2019) + adjuvant | 21 (21/100) | 20 (11/55) |
| 5 plus 1 | 86 (86/100) | 93 (51/55) |
| 5 plus 2 | 81 (81/100) | 82 (45/55) |
| 5 plus 3 | 78 (78/100) | 75 (41/55) |
| 5 plus 4 | 80 (80/100) | 78 (43/55) |

The following study examines the ability of the dLOS-TT conjugate to protect against NTHi infection in a chinchilla model of otitis media This was a randomized, blind, controlled study of active prevention of acute otitis media caused by NTHi in chinchillas which was approved by NINDS/NIDCD ACUC, National Institutes of Health.

Experimental Scheme

Figure 2:
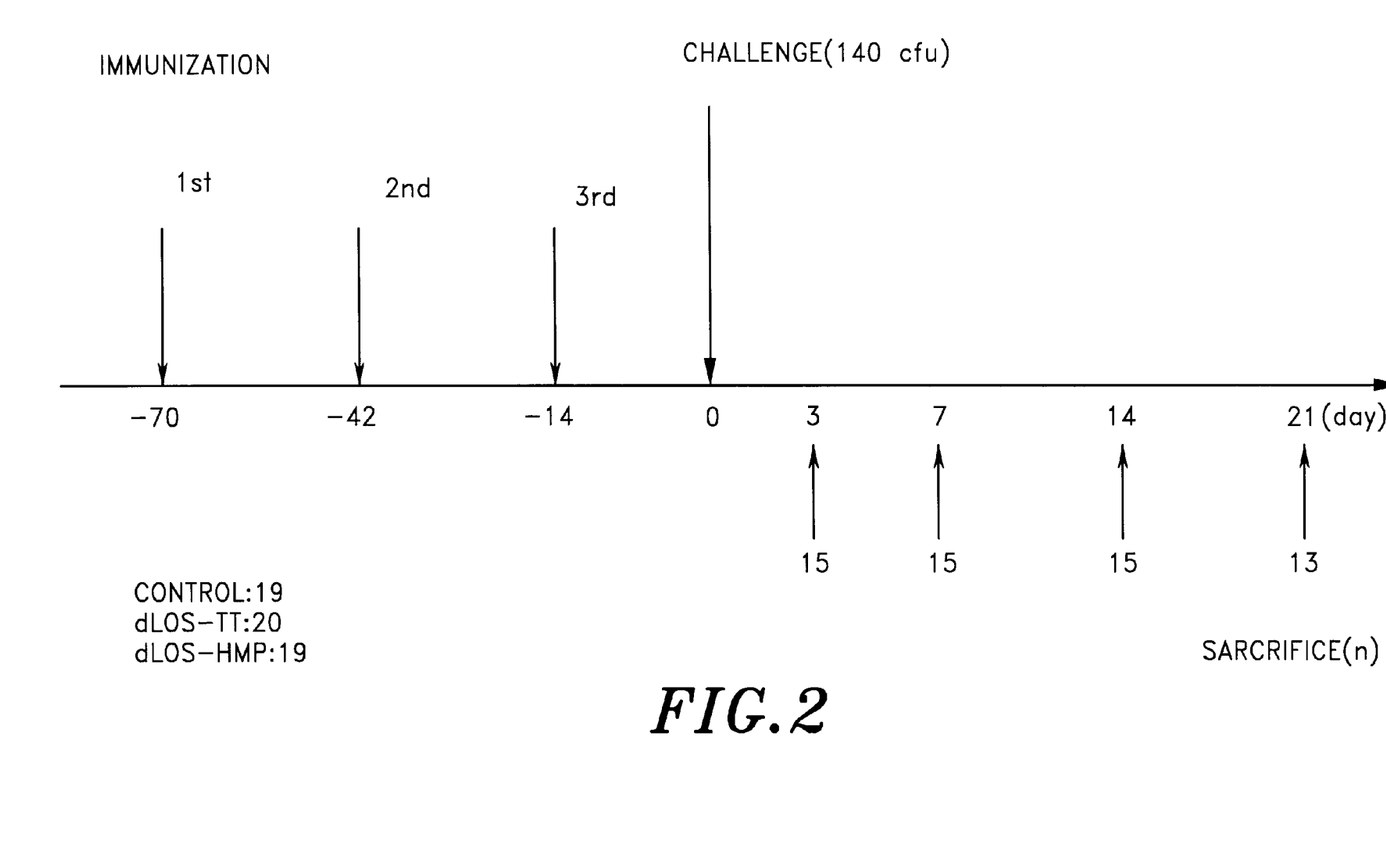
FIG. 2 shows the timetable for administration of the dLOS-TT and dLOS-HMP conjugate vaccines and subsequent NTHi bacterial challenge in the chinchilla model of acute otitis media.

A total of 58 healthy adult chinchillas, weighing between 400 and 600 grams each, were obtained from an outbred ranch (Moulton Chinchilla Ranch, Rochester, Minn.) and housed in separate cages throughout the experiments. All animals were quarantined for one week to acclimate to the laboratory prior to treatment. The animals were randomly assigned to three groups: 1) Control; 2) dLOS-TT; and 3) dLOS-HMP (FIG. 2). A blood sample was obtained from the transverse venous sinus of each chinchilla (Boellcher et al., *Lab. Anim. Sci.*, 40:223–224, 1990). Three days after bleeding, the animals were immunized with three doses of the coded vaccines or saline (control) at four week intervals and challenged with 140 colony forming units (CFU) of NTHi strain 9274 into the right middle ear 14 days after the last immunization (FIG. 2). Both ears were examined daily by otoscopy for evidence of acute otitis media during a period of 21 days after challenge. On day 3, 7, 14 and 21 post-challenge, the animals were sacrificed by overdose ketamine injection and cervical dislocation, and the middle ear fluids (MEFs) from both sides of ears were taken out and cultured for bacterial counting. Blood samples were also collected from all chinchillas 14 days after the first and second immunization, 10 days after the third immunization and before sacrifice. The animals were anaesthetieed with ketamine-HCl (30 mg/kg of body weight, im) prior to all operative procedures.

EXAMPLE 12

Immunization and Middle Ear Challenge

Animals were immunized with 25 μg NTHi 9274 dLOS-TT, dLOS-HMP (dLOS content) or saline in a total volume of 0.3 ml (0.15 ml intramuscularly in the right rear leg and 0.15 ml subcutaneously in the back) for each time (FIG. 2). Conjugates were prepared as described in the previous examples. The composition of dLOS-TT was 150 μg/ml of dLOS and 231 μg/ml of TT with the molar ratio of dLOS to TT at 32: 1, while the composition of dLOS-HMP was 152 μg/ml of dLOS and 223 μg/ml with the molar ratio at 25.5:1. All immunogens were emulsified 1:1 in complete Freund's adjuvant (CFA) for the first and in incomplete Freund's adjuvant (IFA) (Difco, Detroit, Mich.) for the second and third immunizations.

NTHI strain 9274 bacteria were recovered from Greave's solution stocks by transfer of a loopful of thawed organisms to a chocolate agar plate and incubated at 37° C. under 5% $CO_2$ for 16 hours. The next day, 5–10 colonies were transferred to 50 ml of 3% brain-heart infusion (BHI) broth with NAD (5 μg/lml) and hemin (2 μg/ml) (Sigma) in a 250 ml Erlenmeyer flask. Cells were grown for 4–6 hours at 37° C. in a shaker incubator (Model G25, New Brunswick Scientific Co., Edison, N.J.) at 150 rpm. Bacteria in mid-log growth phase ($OD_{600}$=0.5–0.6) were harvested by centrifugation (4,000×g) at 4° C. for 10 minutes, then washed twice with PBS containing 0.5% BSA, 0.15 mM $CaCl_2$ and 0.5 mM $MgCl_2$ (Barenkamp, *Infect. Immum.*, 64:1246–1251, 1996). The washed bacteria were maintained at 4° C. prior to animal challenge.

After anaesthetization, the area over the superior bulla of each animal was shaved and cleaned. Under sterile conditions, 0.2 ml. of approximately 140 CFU bacteria was directly injected into the right middle ear via puncture of the superior aspect of the right cephalic bulla (Giebink, "The experimental otitis media due to *Haemophilus influenzae* in the chinchilla", in *Haemophilus influenzae*, Sell et al., Eds., Elsevier, New York, pp. 73–80, 1982; DeMaria et al., *Infect. Immun.*, 64:5187–5192, 1996, both incorporated by reference) with a 25-gauge needle attached to a 1 ml syringe. This inoculum was predetermined to induce otitis media within 48 hours.

EXAMPLE 13

Otoscope Observations

Animals were examined daily by two operators with otoscope postchallenge. A diagnosis of acute otitis media was made by the linear criterion rating from 0 to 4 scale of middle ear pathology based on the methods of Giebink et al. (*Laryngoscope*, 93:208–211, 1983) and Green et al. (*Meth. Enzymol.*, 235:59–68, 1994), both of which are hereby incorporated by reference, with modifications. A rating of 0 was a normal tympanic membrane (TM) with no pathological change around. A "1" was given if any congestive on the edges of TM was shown but TM was normal. A "2" was rated when severe congestive TM, opaque TM or any indication of minimal pathological changes was present, but TM can be moved by aspiration with the tubulerating. A "3" was assigned when there was evidence of moderate pathological changes, bulging TM, erythema, but no observable air-fluid level or fluids were seen. A "4" was given if any observable air-fluid level, yellow or bloody fluid was seen or TM cannot be moved, or perforation and discharge or substantial effusion volume with signs of severe inflammation were observed. The diagnosis of inner ear infection was made when the aninal had auditory vertigo (Shurin et al., *J. Pediatr.*, 97:364–369, 1980; Giebink et al., supra).

On days 3, 7, 14, and 21 postchallenge, 4–5 chinchillas in each group were sacrificed (FIG. 2) and the superior bullae were opened. MEFs were aspirated from inferior bullae by a 23-gauge needle with suitable angle, then the middle ears were washed with 0.5 ml sterile PBS. The volume, color and consistency of MEFs were recorded. An aliquot of MEFs and their serial dilutions was plated into chocolate agar for a quantitative count of recovered NTHi. All procedures were performed under sterile conditions.

Figure 3:
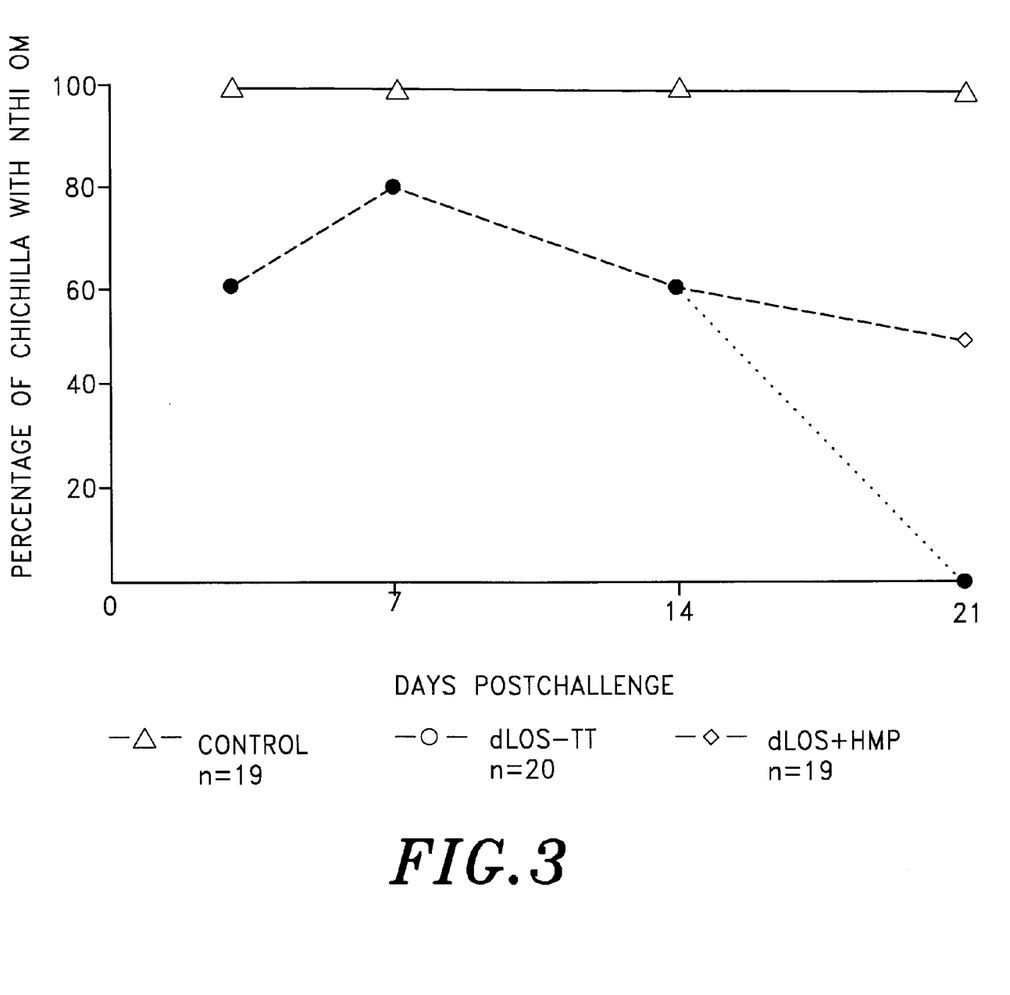
FIG. 3 is a graph showing the percentage of chinchillas with NTHi otitis media up to 21 days postchallenge with NTHi.

All control animals developed NTHi otitis media with effusion from one or both sides of the ears up to 21 days postchallenge. However, in the group administered the conjugate, only 60%, 80% and 60% developed NTHi otitis media with effusion on day 3, 7, and 14, respectively (FIG. 3). On day 21, none of the animals in the dLOS-TT group and only 50% of the animals in the dLOS-HMP group showed otitis media with effusion. The numbers of otitis media with effusion were reduced 78% on day 21 (2/9 vs. 4/4; p=0.02) and 44% on whole course (22/39 vs. 19/19; p=0.0003) in the conjugate group compared to the control group.

The incidence of NTHi culture-positive MEFs from both ears of each group on days 3, 7, 14 and 21 postchallenge is shown in Table 14. The incidence of NTHi culture positive MEFs from total ears was reduced 44% by day 3 (p=0.07), 85% by day 21 (p=0.003), and 46% during the whole course (p=0.0003) in conjugate groups compared to the control group. The incidence of NTHi culture positive MEFs from the left (unchallenged) ear dropped 100% by day 21 (p=0.077), and 51% during the whole course (p=0.04) in the conjugate group relative to the control group. The results from the right ear (challenged ear) were consistent with those of individual animals as mentioned above. There was also a clinical tendency of reduction on other experimental time points but no statistical significance between the conjugate and control groups. The incidence of inner ear infection was also reduced by 51% in the conjugate group (11/39) relative to the control group (11/19) (p=0.029).

TABLE 14

Bacterial culture-positive rates (number of positives/total number) of MEFs from immunized chinchillas challenged with strain 9274

| | Control | | Conjugates (dLOS-TT, dLOS-HMP) | | Total | |
|---|---|---|---|---|---|---|
| | right | left | right | left | control | conjugates |
| Day 3 | 5/5 | 3/5 | 6/10 (3/5[a], 3/5[b]) | 3/10 (1/5, 2/5) | 8/10 | 9/20+ |
| Day 7 | 5/5 | 4/5 | 8/10 (4/5, 4/5) | 5/10 (3/5, 2/5) | 9/10 | 13/20 |
| Day 14 | 5/5 | 1/5 | 6/10 (3/5, 3/5) | 2/10 (1/5, 1/5) | 6/10 | 8/20 |
| Day 21 | 4/4 | 2/4 | 2/9* (0/5, 2/4) | 0/9+ (0/5, 0/4) | 6/8 | 2/18** |
| Total | 19/19 | 10/19 | 22/39*** | 10/39* | 29/38 | 32/78*** |

[a]number of animals having culture-positive MEFs/total number of animals for dLOS-TT-immunized animals;
[b]number of animals having culture-positive MEFs/total number of animals for dLOS-HMP-immunized animals.
Saline vs. conjugate-immunized group: +p = 0.07–0.08; *p < 0.05; p < 0.01; *p < 0.001.

Figure 4:
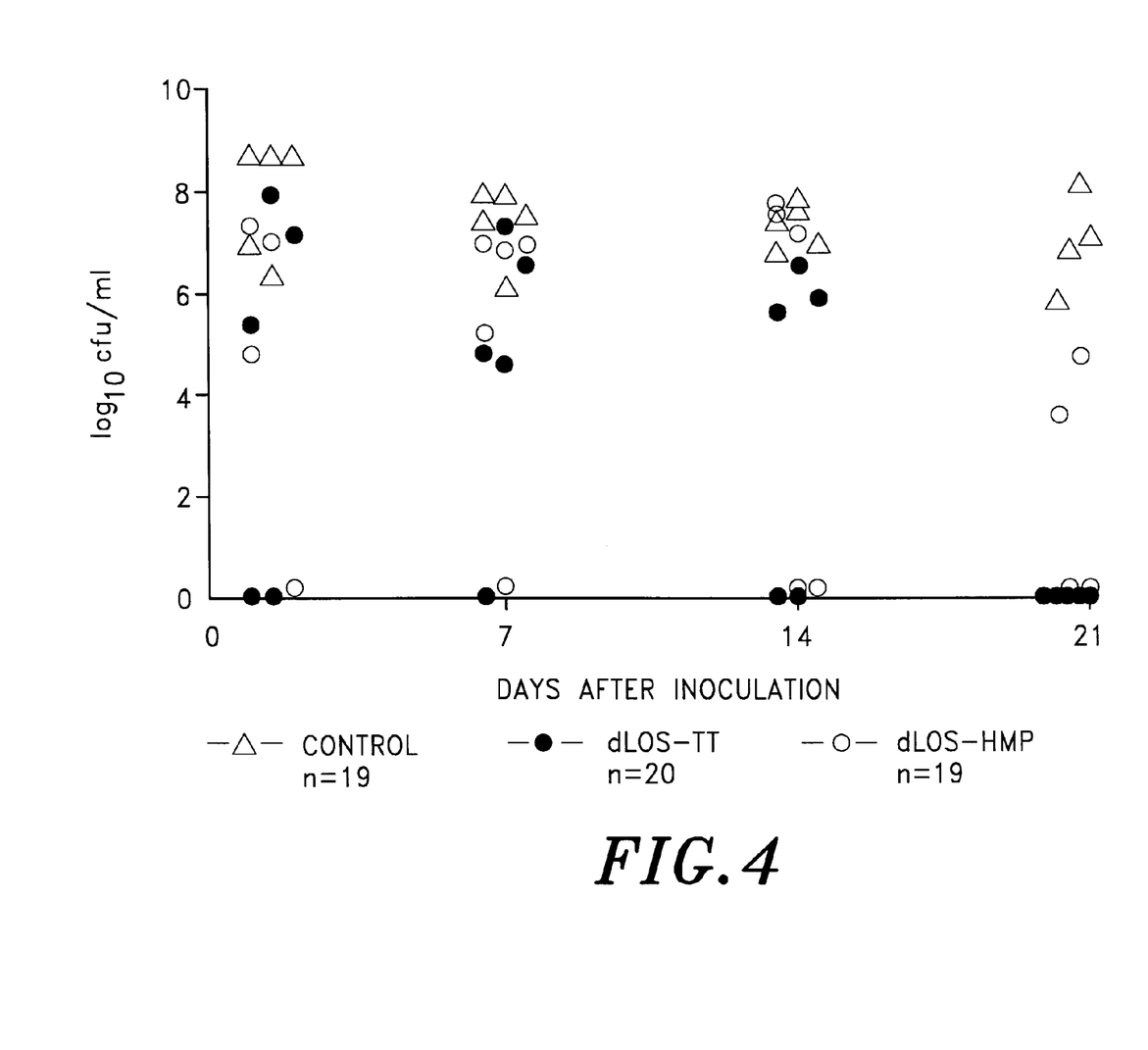
FIG. 4 is a graph showing bacterial counts in middle ear fluids from control and conjugate-immunized chinchillas at 3, 7, 14 and 21 days postchallenge with NTHi.

When quantitative bacterial counts were performed on middle ear fluids recovered from infected animals at the right ear (challenged ear), there were significant differences between the conjugate and the control groups (FIG. 4) on each endpoint day. Conjugate-immunized animals had significantly lower middle ear fluid bacterial counts than did control animals (p=0.003).

Figure 5:
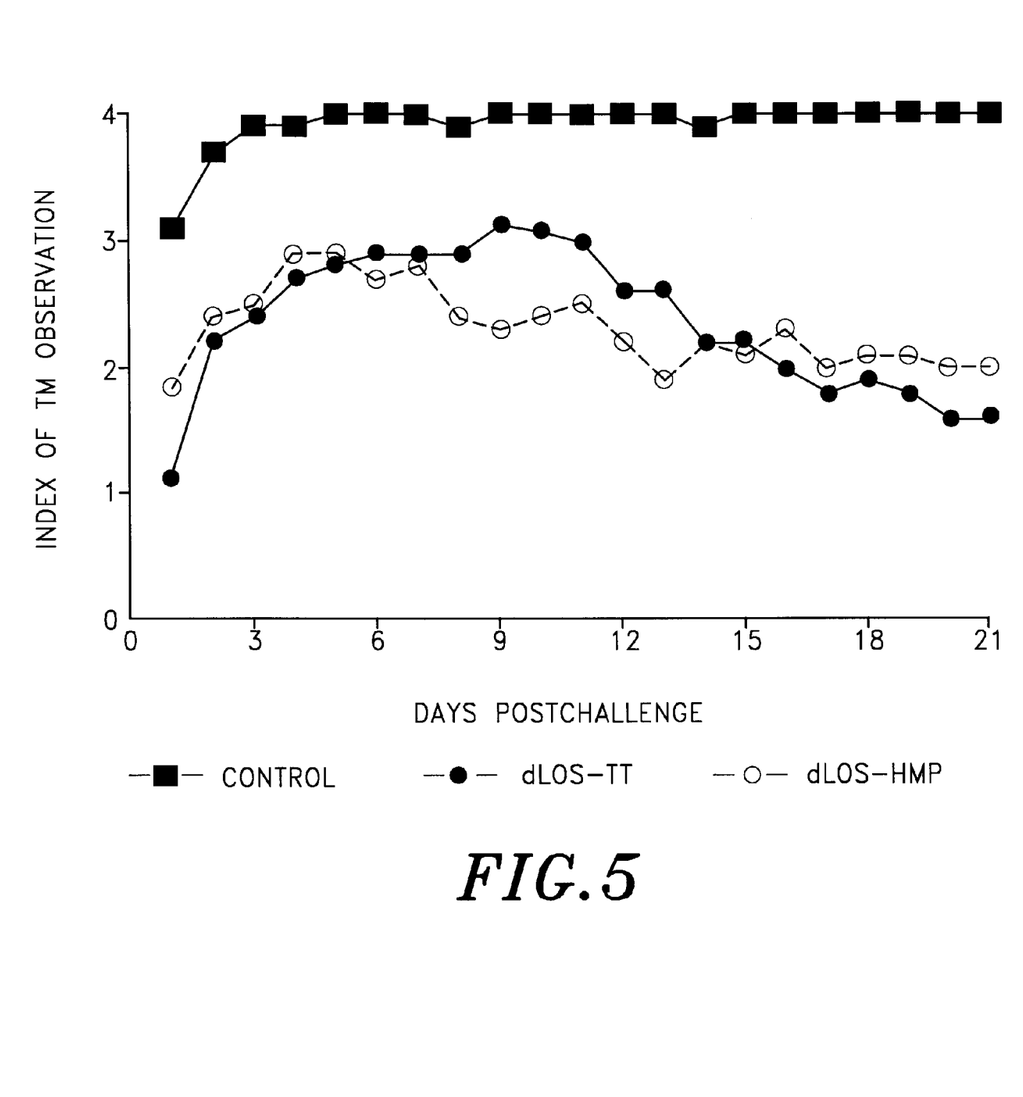
FIG. 5 is a graph showing the index of tympanic membrane observation (TM) in control and conjugate-immunized chinchillas up to 21 days postchallenge with NTHi. The higher the index of TM observation, the more severe the otitis media.

Tympanic membrane observation of right (or challenge) ears by otoscopy showed signs of acute otitis media on day 1 postchallenge in the majority of animals. However, much more severe signs of infection were observed in the control group (average rating of 3.1±0.8) versus the dLOS-TT (1.1±1.2) or dLOS-HNT (1.8±1.4) groups (FIG. 5). By day 2, approximately 90% of control animals, but only 40% of conjugate-immunized animals, had a rating of 4. By day 4, all control animals showed severe signs of infection with a rating of 4 which remained up to day 21 (FIG. 5). In contraat, only about 55% of conjugate-immunized animals had a rating of 4 by day 4 and the maximum percentage of the highest rating at 4 was about 65% between days 5 and 11. By day 13, the conjugate-immunized animals showed apparent clearance of infection, with about 60% and 50% of dLOS-TT-immunized and dLOS-HMP-immunized, respectively, animals recovering from infection by day 21. The average numbers of TM observations were 4±0, 1.6±1.1, and 2±1.6 by day 21 (p<0.001), and 3.6±0.6, 2.5±1.9 and 2.8±1.6 at the whole period of 21 days (p<0.05) for saline, dLOS-TT and dLOS-HMP, respectively. Similar results were also obtained from left (or non-challenge) ears.

EXAMPLE 14

Immunozenicity of Coniugates in Chinchillas

Serum antibodies to NTHi 9274 LOS were determined by ELISA (Barenkamp, *Infect. Immun.*, 64:1246–1251, 1996; Gu et al., *Infect. Immun.*, 64:4047–4053, 1996). Briefly, 96-well plates were coated with 10 μg/ml LOS solution in PBS, pH 7.4 containing 0.1 mM $MgCl_2$ overnight at 4° C. The plates were washed and blocked with 5% fetal calf serum (FCS) in PBS for 1 hour, diluted sera were added and the mixtures were incubated for 2 hours. For IgG+IgM, rabbit anti-chinchilla IgG/IgM sera (1:500) (Barenkamp et al., supra) were added, and each mixture was incubated for 1 hour. For chinchilla IgG, protein A-alkaline phosphatase conjugate (Sigma) was added and the mixture was incubated for 1 hour. All steps were preformed at room temperature and PBS containing 0.05% Tween-20 was used in five washings between steps. Diluents for sera and conjugates were PBS containing 5% FCS and 0.05% Tween-20. Enzyme substrates were added for 30 minutes and the reactions were read with a microplate autoreaded (Bio-Tek Instruments Model EL311) at $A_{405}$. A chinchilla antisera raised against LOS was used as a positive control for each plate. Negative controls included buffer, alkaline phosphatase conjugate and serum alone. All negative controls gave optical density readings of less than 0.3. Chinchilla serum antibodies to TT or HMP were also measured by a similar ELISA to that described above, except TT or HMP was used as a coating antigen (5 μg/ml in 0.1 M Tris buffer, pH 9.8).

Three immunizations of saline did not elicit a rise of LOS antibodies in control chinchillas (Table 15). In contrast, both conjugates elicited significant levels of LOS antibodies with a 60- to 70-fold increase in IgG+IgM and a 20- to 40-fold increase in IgG after one injection. Increases of about 100-fold for IgG+IgM and 100- to 200-fold for IgG after three injections (P<0.001) were observed. IgG levels elicited by dLOS-TT were higher than those elicited by dLOS-HMP after three injections (p=0.0506). There was a negative correlation between LOS-IgG antibody levels and the bacterial counts of middle ear fluids among all 58 animals (r=−0.298, P=0.023).

TABLE 15

Chinchilla antibody response to NTHi 9274 LOS elicited by conjugates

| | Bleeding | GM (± SD range) ELISA titers for | |
|---|---|---|---|
| Immunogen | No. | IgG + IgM | IgG |
| Saline | 1 | 33 (18~60) | 11 (8~16) |
| | 2 | 35 (20~61) | 12 (8~18) |
| | 3 | 36 (22~60) | 13 (8~20) |

TABLE 15-continued

Chinchilla antibody response to NTHi 9274 LOS elicited by conjugates

| Immunogen | Bleeding No. | GM (± SD range) ELISA titers for | |
|---|---|---|---|
| | | IgG + IgM | IgG |
| | 4 | 38 (24~60) | 12 (8~18) |
| | 5 | 38 (24~60) | 12 (8~18) |
| dLOS-TT | 1 | 30 (17~54) | 16 (9~27) |
| | 2 | 1950 (579~6566) | 726 (88~5959) |
| | 3 | 3771 (1430~9943) | 1951 (403~9451) |
| | 4 | 3984 (1730~9173) | 3378 (1088~10932) |
| | 5 | 3157 (1248~8902) | 2865 (822~9989) |
| dLOS-HMP | 1 | 34 (17~67) | 13 (8~20) |
| | 2 | 2431 (588~10044) | 321 (40~2571) |
| | 3 | 3643 (1069~12431) | 764 (120~4853) |
| | 4 | 2430 (567~10418) | 1214 (174~8490) |
| | 5 | 2292 (597~8792) | 1286 (237~6978) |

[a]58 chinchillas were immunized subcutaneously and intramuscularly with 3 doses of saline, dLOS-TT, or dLOS-HMP at 4-week intervals.
[b]blood samples were collected before (No. 1), 2 weeks after the 1st and 2nd immuniztion (No. 2 and 3), 10 days after the 3rd immunization (No. 4), and before sacrifice (No. 5).
[c]saline-immunized sera or presera vs. conjugate-immunized sera: p < 0.001. There is no significant difference between dLOS-TT and dLOS-HMP except * vs. **: p = 0.0506.

Antibody responses to TT or HMP are shown in Table 16. Saline did not elicit TT or HMP antibodies. In contrast, both conjugates elicited significant levels of protein antibodies (IgG) with an approximate 300- to 1,400-fold increase after one injection and a 3,000- to 4,000-fold increase after three injections (p<0.001). Low levels of IgM were detected since the levels of IgG+IgM were similar to that of IgG only.

TABLE 16

Chinchilla antibody response to TT and HMP elicited by NTHi 9274 dLOS conjugates

| Immunogen[a] | Bleeding No.[b] | GM (± range) ELISA Titers for: | |
|---|---|---|---|
| | | TT | HMP |
| Control | 1 | 21 (14~35) | 17 (14~44) |
| | 2 | 22 (17~29) | 26 (19~57) |
| | 3 | 25 (16~37) | 22 (14~51) |
| | 4 | 24 (19~41) | 31 (17~56) |
| | 5 | 26 (16~34) | 24 (19~50) |
| dLOS-TT | 1 | 26 (18~37) | —[c] |
| | 2 | 7,665 (2,177~26,990) | — |
| | 3 | 65,313 (25,609~166,571) | — |
| | 4 | 81,358 (40,243~164,475) | — |
| | 5 | 55,387 (20,375~150,557) | — |
| dLOS-HMP | 1 | — | 34 (22~54) |
| | 2 | — | 48,638 (16,007~147,741) |
| | 3 | — | 97,342 (47,490~199,526) |
| | 4 | — | 163,757 (99,609~269,215) |
| | 5 | — | 183,865 (121,815~277,524) |

[a], [b]: See Table 15 footnote.
[c]: not done

EXAMPLE 15

Chinchilla Antibody Bactericidal Assay

Chinchilla pre- and postimmune sera (after three injections) were inactivated at 56° C. for 30 minutes and tested for bactericidal activity against NTHi 9274 by a microbactericidal assay (Gu et al., Infect. Immun., 64:4047–4053, 1996). Briefly, a five-fold dilution of the initial sera, then two-fold serial dilutions were made in PBS containing calcium, magnesium and 0,1% gelatin (DPBSG), so that 50 μl of diluted sera was present in each well of a 96-well plate. Strain 9274 was grown on chocolate agar plates at 37° C. under a 5% $CO_2$ atmosphere overnight, and three to five colonies were transferred to another plate and incubated for 4–5 hours. The bacterial were diluted in DPBSG and 30 μl of bacterial suspension (about $3\times10^3$ CFU/ml) was added to each well. Infant rabbit serum (20 μl/well) was added as a source of complement (Pel-freez). The plates were incubated at 37° C. for 45 minutes. Subsequendy, 50 μl of the mixture was transferred from each well onto chocolate agar plates. The plates were incubated at 37° C. under 5% $CO_2$ overnight and colonies were counted. Controls included complement, inactivated complement and a positive serum sample. The highest serum dilution caused >50% killing and was expressed as the reciprocal of bactericidal titer.

Neither presera not saline immunized sera showed bactericidal activity. However, 53% or 49% of dLOS-TT or dLOS-HMP immunized sera demonstrated a complement-mediated bactericidal activity against strain 9274 (Table 17). The titers ranged from 1:10 to 1:160. There was a positive correlation between LOS-IgG antibody levels (ELISA) and the bactericidal titers among all 58 animals.

TABLE 17

Bactericidal activity of chinchilla antisera elicited by NTHi 9274 conjugates

| Immunogen[a] | GM (± SD range) bactericidal titers[b] | | Positive Rate (%) |
|---|---|---|---|
| | Presera | 3rd immunized sera | |
| Saline Control | <1:5 | <1:5 | 0 (0/19)[c] |
| dLOS-TT | <1:5 | 1:43 (18 ~ 104) | 45 (9/20) |
| dLOS-HMP | <1:5 | 1:46 (17 ~ 128) | 53 (10/19) |
| Conjugates[d] | <1:5 | 1:45 (18 ~ 114) | 49 (19/39) |

[a]See Table 15, footnote.
[b]Reciprocal of the highest dilution of sera showed >50% of killing to NTHi strain 9274.
[c]Saline vs. dLOS-TT or dLOS-HMP: P < 0.001.
[d]dLOS-TT group plus dLOS-HMP group.

Antibody levels are expressed as the geometric mean ELISA titers (reciprocal) of n independent observations ±standard deviation (SD). The MEF bacterial densities are expressed as the geometric CFU mean of n independent observations ±SD. The outcome of otoscopic observation is expressed as the mean of n independent observations ±SD at each time point. The significant differences of the above descriptions between the control and conjugate groups were tested with the student t test. The Fisher's exact test was employed to compare the proportion of infected animals between the control and conjugate groups.

EXAMPLE 16

Immunization of Humans with dLOS-TT Conjugate

Individuals are intramuscularly administered either 25 μg of the conjugate dLOS-TT or dLOS-HEW vaccine prepared as described in Examples 1–4 or a control vaccine. Boosters of 20 μg of conjugate or control vehicle are intramuscularly administered at 2, 4 and 15 months after the initial injection. Immunogenicity and bactericidal activity of the resulting antisera are determined in accordance with Examples 6 and 9. The frequency of occurrence of middle ear infections is then monitored over several years. The individuals receiving the conjugate vaccine have significantly fewer episodes of otitis media than the control subjects.

Multivalent vaccines comprising mixtures of dLOSs from different NTHi strains may also be used, particularly dLOSs from those strains which cause the most infections in humans.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A conjugate vaccine for nontypeable *Haemophilus influenzae* (NTHi), comprising lipooligosaccharide (LOS) from which esterified fatty acids have been removed from lipid A to form detoxified LOS (dLOS), and an immunogenic carrier covalently linked thereto.

2. The vaccine of claim 1, wherein said immunogenic carrier is a protein.

3. The vaccine of claim 2, wherein said immunogenic carrier protein is selected from the group consisting of tetanus toxin/toxoid, NTHi high molecular weight protein, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, and respiratory syncytial virus F and G protein.

4. The vaccine of claim 3, wherein said immunogenic carrier protein is tetanus toxod or NTHi high molecular weight protein.

5. A conjugate vaccine for nontypeable *Haemophilus influenzae* (NTHi), comprising lipooligosaccharide (LOS) from which esterified fatty acids have been removed from lipid A to form detoxified LOS (dLOS), and an immunogenic carrier covalently linked thereto via a linker.

6. The vaccine of claim 5, wherein said linker is selected from the group consisting of adipic acid dihydrazide, ε-aminohexanoic acid, chlorohexanol dimethyl acetal, D-glucuronolactone and p-nitrophenylethyl amine.

7. The vaccine of claim 6, wherein said linker is adipic acid dihydrazide.

8. Isolated nontypeable *Haemophilus influenzae* (NTHi) lipooligosaccharide (LOS) detoxified by removal of ester-linked fatty acids from lipid A to form detoxified LOS (dLOS) coniugated to a carrier.

9. A pharmaceutical composition comprising the vaccine conjugate of claim 1 in a pharmaceutically acceptable carrier.

10. The pharmaceutical composition of claim 9, further comprising an adjuvant.

11. The pharmaceutical composition of claim 10, wherein said adjuvant is alum.

12. The conjugate vaccine of claim 1, wherein said esterified fatty acids have been removed by treatment with hydrazine.

13. The conjugate vaccine of claim 1, wherein said dLOS is at least about 5,000 fold less toxic than said lipooligosaccharide as determined using the limulus amebocyte lysate (LAL) assay.

14. The conjugate vaccine of claim 5, wherein said esterified fatty acids have been removed by treatment with hydrazine.

15. The conjugate vaccine of claim 5, wherein said dLOS is at least about 5,000 fold less toxic than said lipooligosaccharide as determined using the limulus amebocyte lysate (LAL) assay.

16. The dLOS of claim 8, wherein said ester-linked fatty acids have been removed by treatment with hydrazine.

17. The dLOS of claim 8, wherein said dLOS is at least about 5,000 fold less toxic than said lipooligosaccharide as determined using the limulus ameboctye lysate (LAL) assay.

18. The conjugate vaccine of claim 1, wherein said dLOS is at least about 10,000 fold less toxic than said lipooligosaccharide as determined using the limulus amebocyte lysate (LAL) assay.

19. The conjugate vaccine of claim 5, wherein said dLOS is at least about 10,000 fold less toxic than said lipooligosaccharide as determined using the limulus amebocyte lysate (LAL) assay.

20. The dLOS of claim 8, wherein said dLOS is at least about 10,000 fold less toxic than said lipooligosaccharide as determined using the limulus amebocyte lysate (LAL) assay.

* * * * *